United States Patent
Oda et al.

(10) Patent No.: US 9,618,363 B2
(45) Date of Patent: Apr. 11, 2017

(54) SPECIMEN ANALYSIS SYSTEM, SPECIMEN ANALYZER, AND SPECIMEN ANALYSIS METHOD

(71) Applicant: Sysmex Corporation, Kobe-shi, Hyogo (JP)

(72) Inventors: Tetsuya Oda, Kobe (JP); Keisuke Kuwano, Kobe (JP); Daigo Fukuma, Kobe (JP); Shunsuke Ariyoshi, Kobe (JP)

(73) Assignee: SYSMEX CORPORATION, Kobe-Shi, Hyogo (JP)

( * ) Notice: Subject to any disclaimer, the term of this patent is extended or adjusted under 35 U.S.C. 154(b) by 219 days.

(21) Appl. No.: 13/958,050

(22) Filed: Aug. 2, 2013

(65) Prior Publication Data

US 2013/0317773 A1    Nov. 28, 2013

Related U.S. Application Data

(63) Continuation of application No. PCT/JP2012/052008, filed on Jan. 30, 2012.

(30) Foreign Application Priority Data

Feb. 3, 2011   (JP) ................ 2011-022100

(51) Int. Cl.
*G01D 3/00* (2006.01)
*G01N 35/00* (2006.01)
*G01N 35/04* (2006.01)
*G06F 19/00* (2011.01)

(52) U.S. Cl.
CPC ......... *G01D 3/00* (2013.01); *G01N 35/00594* (2013.01); *G01N 35/00603* (2013.01); *G06F 19/366* (2013.01); *G01N 2035/0472* (2013.01); *G05B 2219/45092* (2013.01)

(58) Field of Classification Search
CPC ................................ G01N 35/00603
(Continued)

(56) References Cited

U.S. PATENT DOCUMENTS 5,100,622 A * 3/1992 Mimura ........... G01N 35/00594
356/73
2003/0127340 A1   7/2003 Dilger
(Continued)

FOREIGN PATENT DOCUMENTS

JP   05-232123 A   9/1993
JP   07-120471 A   5/1995
(Continued)

OTHER PUBLICATIONS

International Search Report for International Application No. PCT/JP2012/052008, dated Mar. 6, 2012, 2 pages.

*Primary Examiner* — Gregory J Toatley
*Assistant Examiner* — Michael Dalbo
(74) *Attorney, Agent, or Firm* — Brinks Gilson & Lione

(57) ABSTRACT

A specimen analysis system, a specimen analyzer, and a specimen analysis method are provided by which reexamination of a specimen can be executed more quickly than in conventional technology. A specimen analyzer measures a specimen and obtains an analysis result. The specimen analyzer determines the necessity of remeasurement of the specimen, based on a specimen analysis result. Also, the specimen analyzer determines, based on the specimen analysis result, whether or not determination of the necessity of remeasurement of the specimen based on examination information by the examination information management device is necessary. If it is determined that determination of the necessity of remeasurement of the specimen based on the examination information is necessary, the specimen analyzer makes a request to determine the necessity of remeasure- (Continued)

ment of the specimen based on the examination information, to the examination information management device.

20 Claims, 20 Drawing Sheets

(58) Field of Classification Search
USPC .......................................... 702/22, 31, 104
See application file for complete search history.

(56) References Cited

U.S. PATENT DOCUMENTS

| | | | |
|---|---|---|---|
| 2005/0036912 A1* | 2/2005 | Yamakawa et al. | 422/65 |
| 2007/0038406 A1* | 2/2007 | Uemura et al. | 702/127 |
| 2007/0233518 A1* | 10/2007 | Tanaka et al. | 705/2 |
| 2010/0159603 A1* | 6/2010 | Hamada et al. | 436/47 |
| 2010/0212438 A1* | 8/2010 | Tanaka | G01N 35/026 73/864.81 |
| 2010/0248293 A1* | 9/2010 | Kuwano et al. | 435/29 |
| 2010/0248374 A1* | 9/2010 | Kitagawa et al. | 436/47 |

FOREIGN PATENT DOCUMENTS

| | | |
|---|---|---|
| JP | 2003-004750 A | 1/2003 |
| JP | 2005-515438 A | 5/2005 |
| JP | 2007-271331 A | 10/2007 |
| JP | 2010-169663 A | 8/2010 |
| JP | 2010-256260 A | 11/2010 |
| JP | 2010-256325 A | 11/2010 |

* cited by examiner

FIG. 20

| Specimen number | Output P/N | Action | Order type | Error | Discrete | Rule result | Specimen comment |
|---|---|---|---|---|---|---|---|
| 123456789 | DGH MC | | Initial | | CBC-DIFF | QueryToHost | |
| 6302501 | DGH | | Initial | | CBC-DIFF | | |
| 987654321 | DGH | | Initial | | CBC-DIFF | Reflex(1) | |
| 5682701 | DGH D C | | Initial | | CBC-DIFF | | |
| 456123789 | DGH DMC | | Initial | | CBC-DIFF | | |

| ITEM | DATE | UNIT |
|---|---|---|
| WBC | 30.4 | 10^2/uL |
| RBC | 4612 | 10^4/uL |
| HGB | 9.3 | g/dL |
| HCT | 30.5 | % |
| MCV | 95.9 | fL |
| MCH | 29.2 | pg |
| MCHC | 30.5 | g/dL |
| PLT | 17.0 | 10^4/uL |
| RDW-SD | 86.6 | fL |
| RDW-CV | 23.4 | % |
| PDW | 11.0 | fL |
| MPV | 10.1 | fL |
| P-LCR | 26.2 | % |
| PCT | 0.17 | % |
| NRBC# | 0.1 | 10^2/uL |
| NRBC% | 0.3 | % |
| NEUT# | 20.6 | 10^2/uL |
| LYMPH# | 9.3 | 10^2/uL |
| MONO# | 3.5 | 10^2/uL |
| EO# | 0.4 | 10^2/uL |
| BASO# | 0.2 | 10^2/uL |
| NEUT% | 60.5 | % |
| LYMPH% | 27.4 | % |
| MONO% | 10.3 | % |
| EO% | 1.2 | % |
| BASO% | 0.6 | % |
| IG# | 0.3 | 10^2/uL |
| IG% | 0.9 | % |
| RET# | | 10^4/uL |
| RET% | | % |
| IRF | | % |
| LFR | | % |
| MFR | | % |
| HFR | | % |
| RET-He | | pg |

SPECIMEN ANALYSIS SYSTEM, SPECIMEN ANALYZER, AND SPECIMEN ANALYSIS METHOD

RELATED APPLICATIONS

This application is a continuation of PCT/JP2012/052008 filed on Jan. 30, 2012, which claims priority to Japanese Application No. 2011-022100 filed on Feb. 3, 2011. The entire contents of these applications are incorporated herein by reference.

BACKGROUND OF THE INVENTION

1. Field of the Invention

The present invention relates to a specimen analysis system, a specimen analyzer, and a specimen analysis method for analyzing a specimen.

2. Description of the Related Art

Conventionally, specimen analyzers for analyzing a specimen such as blood or urine are known. For example, Japanese Unexamined Patent Application Publication No. H7-120471A discloses an automatic analyzer including an analysis unit for analyzing a patient specimen and a data processing unit for receiving a measurement result from the analysis unit and checking data. The data processing unit of the automatic analyzer described in H7-120471A is capable of communicating with a superordinate computer, and has a function of receiving previous value data of a patient from the superordinate computer. The data processing unit performs data check, such as comparing the previous value data with current value data of the patient, and determines whether or not remeasurement (reexamination) is necessary.

As the superordinate computer described in H7-120471A mentioned above, usually, an examination information management device is used that is called a LIS (Laboratory Information System) or a WAM (Working Area Manager) and is communicably connected to a plurality of specimen analyzers. To manage the progress of general clinical examination procedures, the aforementioned examination information management device is connected to a large number of automatic analyzers and terminals via a network. With the automatic analyzer described in H7-120471A, it is necessary to request the previous value data from the superordinate computer (examination information management device) at every specimen measurement, and determine the necessity of remeasurement, using the previous value data received from the examination information management device.

SUMMARY OF THE INVENTION

The scope of the present invention is defined solely by the appended claims, and is not affected to any degree by the statements within this summary.

A first aspect of the present invention is a specimen analysis system according to an aspect of the present invention is a specimen analysis system including: an examination information management device for managing examination information regarding examination of a specimen; and a specimen analyzer for measuring the specimen and transmitting a measurement result to the examination information management device, the specimen analyzer including: a measurement unit configured to measure the specimen; a storage unit configured to store a predetermined determination condition; and a control unit that is capable of executing query processing for making a query to the examination information management device about whether or not remeasurement of the specimen is necessary and determination processing for determining whether or not the measurement result matches the predetermined determination condition that is stored in advance in the storage unit, wherein the control unit causes the measurement unit to execute remeasurement of the specimen and for transmitting a measurement result of the remeasurement to the examination information management device in a case where the measurement result matches the predetermined determination condition as a result of execution of the determination processing, and the control unit causes the measurement unit to execute remeasurement of the specimen in a case of receiving, from the examination information management device, determination information indicating that remeasurement of the specimen is necessary as a result of execution of the query processing.

A second aspect of the present invention is a specimen analyzer that is communicably connected to an examination information management device for managing examination information regarding examination of a specimen and that transmits a result of measurement of the specimen to the examination information management device, including: a measurement unit configured to measure the specimen; a storage unit configured to store a predetermined determination condition; and a control unit that is capable of executing query processing for making a query to the examination information management device about whether or not remeasurement of the specimen is necessary and determination processing for determining whether or not the measurement result matches the predetermined determination condition that is stored in advance in the storage unit, wherein the control unit causes the measurement unit to execute remeasurement of the specimen and for transmitting a measurement result of the remeasurement to the examination information management device in a case where the measurement result matches the predetermined determination condition as a result of execution of the determination processing, and the control unit causes the measurement unit to execute remeasurement of the specimen in a case of receiving, from the examination information management device, determination information indicating that remeasurement of the specimen is necessary as a result of execution of the query processing.

A third aspect of the present invention is a specimen analysis method for analyzing a specimen using a specimen analyzer that is communicably connected to an examination information management device for managing examination information regarding examination of the specimen, the method including: a step in which the specimen analyzer transmits a measurement result acquired by measuring the specimen to the examination information management device; a step in which the specimen analyzer determines whether or not the measurement result matches a predetermined determination condition that is stored in advance in the specimen analyzer; step in which in a case where the measurement result matches the predetermined determination condition, the specimen analyzer executes remeasurement of the specimen and transmits a measurement result of the remeasurement to the examination information management device; a step in which in a case where the measurement result does not match the predetermined determination condition, the specimen analyzer makes a query to the examination information management device about whether or not remeasurement of the specimen is necessary; and a step in which in a case of receiving determination information indicating that remeasurement of the specimen is necessary from the examination information management device, the specimen analyzer executes remeasurement of the specimen.

BRIEF DESCRIPTION OF THE DRAWINGS

FIG. 20 is a diagram showing an example of a specimen information list screen.

DETAILED DESCRIPTION OF THE PREFERRED EMBODIMENTS

Preferred embodiments of the present invention will now be described below with reference to the accompanying drawings.

[Configuration of Specimen Analysis System]

Figure 1:
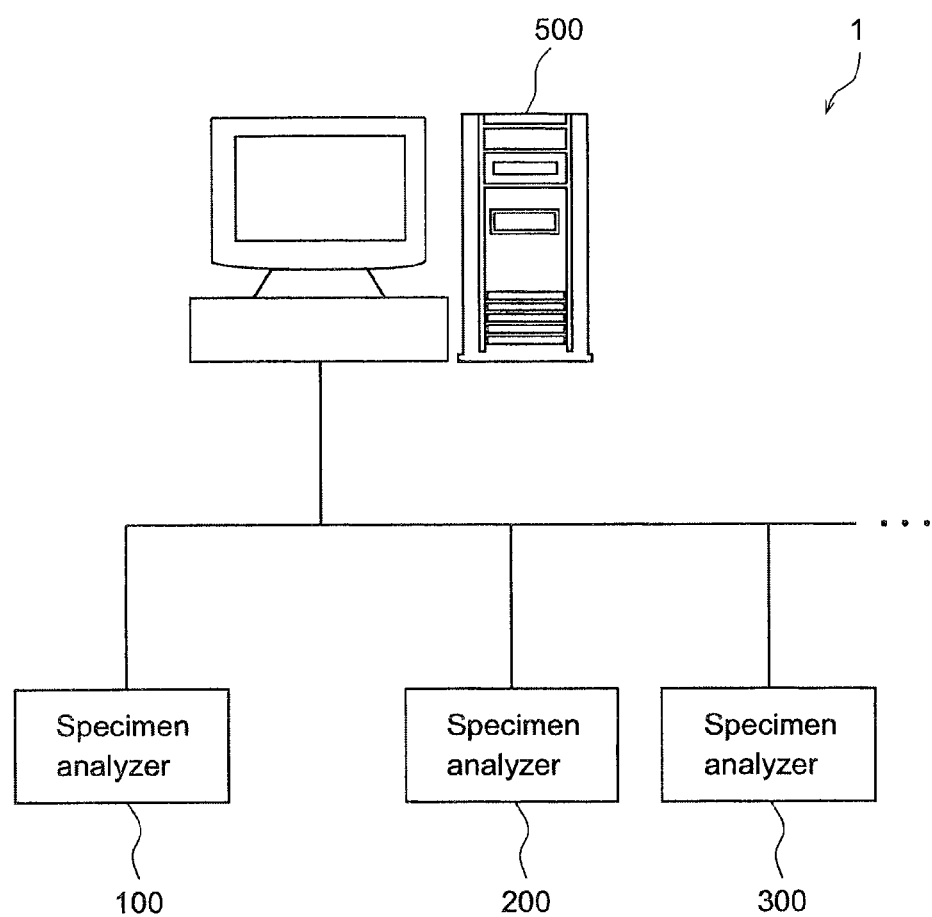
FIG. 1 is a schematic diagram showing an overall configuration of a specimen analysis system according to an embodiment.

FIG. 1 is a schematic diagram showing an overall configuration of a specimen analysis system according to the present embodiment. A specimen analysis system 1 according to the present embodiment is a system for analyzing a specimen (blood specimen, urine specimen, etc.) collected from a patient. The specimen analysis system 1 includes a plurality of specimen analyzers 100, 200, 300, and so on. The specimen analyzer 100 is a multichannel blood cell counter that classifies blood cells contained in a blood specimen into white blood cells, red blood cells, platelets, and the like, and counts the number of blood cells of each type. The specimen analyzer 200 is a blood coagulation measurement device, and the specimen analyzer 300 is a biochemical analyzer. Thus, the specimen analysis system 1 has multiple types of specimen analyzers.

Also, as shown in FIG. 1, the specimen analysis system 1 includes an examination information management device 500 for managing examination information related to a specimen handled by the specimen analysis system. The examination information management device 500 is a device called a LIS (Laboratory Information System) or a WAM (Working Area Manager), and is communicably connected to the specimen analyzers 100, 200, 300, and so on, via a LAN. Specimen analysis results are transmitted from the specimen analyzers 100, 200, 300, and so on to the examination information management device 500, and the examination information including these analysis results is stored in the examination information management device 500.

<Configuration of Specimen Analyzer>

Figure 2:
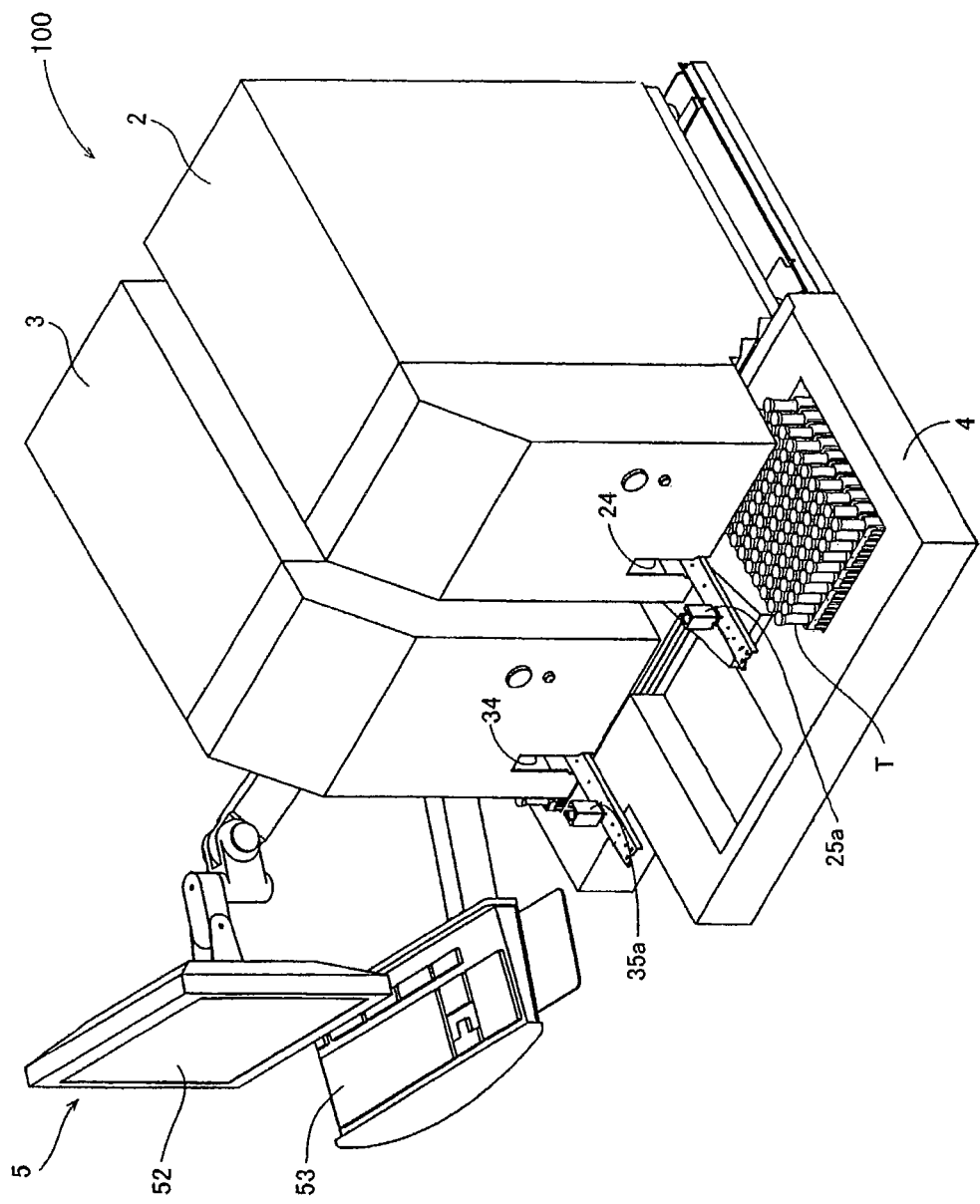
FIG. 2 is a perspective view showing an overall configuration of a specimen analysis system according to an embodiment.

FIG. 2 is a perspective view showing a configuration of the specimen analyzer 100 shown in FIG. 1. The specimen analyzer 100 according to the present embodiment includes two measurement units 2 and 3, a specimen carrying unit 4 disposed on the front side of the measurement units 2 and 3, and an information processing unit 5 that is capable of controlling the measurement units 2 and 3 and the specimen carrying unit 4. Also, for this specimen analyzer, the number of measurement units to be mounted can be set arbitrarily. A configuration in which two measurement units are mounted as shown in FIG. 2 is possible, and a configuration in which one measurement unit is mounted is also possible.

Also, as will be described later, models of the measurement unit 2 and the measurement unit 3 shown in FIG. 2 are different. In other words, in this specimen analyzer, two measurement units 2 and 3 of different models can be mounted. Also, in this specimen analyzer, two measurement units of the same model can be mounted.

<Configuration of Measurement Unit>

Figure 3:
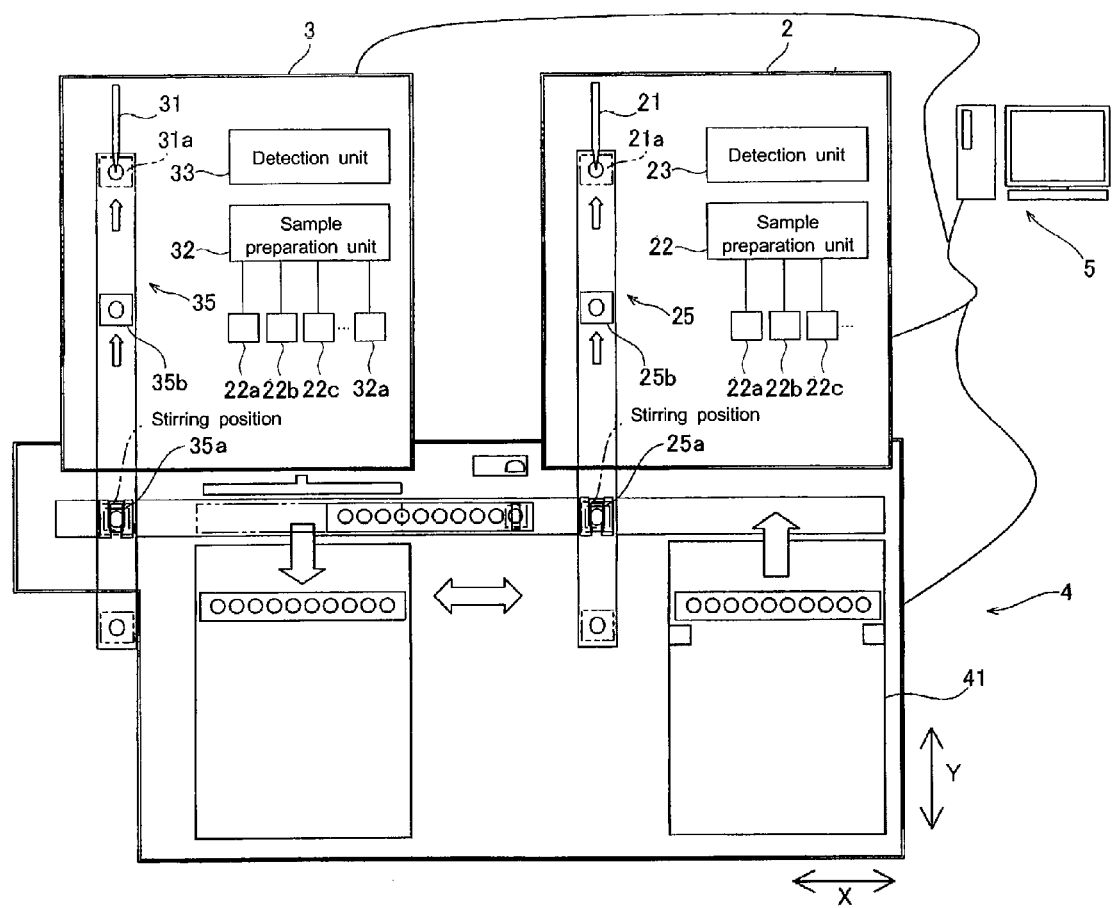
FIG. 3 is a schematic diagram showing a configuration of the specimen analyzer shown in FIG. 2.

FIG. 3 is a schematic diagram showing a configuration of the specimen analyzer 100 shown in FIG. 2. The measurement unit 2 is disposed on the upstream side in a specimen carrying direction (X direction shown in FIG. 3) in the specimen carrying unit 4, and the measurement unit 3 is disposed on the downstream side in this carrying direction. As shown in FIG. 3, the measurement unit 2 has a specimen suction unit 21 for suctioning blood, which is the specimen, from a specimen container (blood-collecting vessel) T, a sample preparation unit 22 for preparing a measurement sample used in measurement of blood constituents such as blood cells, using the blood suctioned by the specimen suction unit 21, and a detection unit 23 for detecting (measuring) blood cells from the measurement sample prepared by the sample preparation unit 22. Also, the measurement unit 2 further has an intake 24 (see FIG. 2) for taking the specimen container T accommodated in a specimen rack L carried by the specimen carrying unit 4 into the measurement unit 2, and a specimen container carrying unit 25 for taking the specimen container T from the specimen rack L into the measurement unit 2 and carrying the specimen container T up to the position of suction by the specimen suction unit 21.

As shown in FIG. 3, a suction tube (not shown) is provided at the tip of the specimen suction unit 21. Also, the specimen suction unit 21 is movable in the vertical direction, and is configured to be moved downward such that the suction tube penetrates a lid portion of the specimen container T that has been carried up to the suction position, and suctions the blood inside.

The sample preparation unit 22 includes a plurality of reaction chambers (not shown). Also, the sample preparation unit 22 is connected to a plurality of reagent containers including a reagent container 22a accommodating a reagent (diluent) for detection of RBC (red blood cell) and PLT (platelet), a reagent container 22b accommodating a reagent for detection of HGB (hemoglobin), a reagent container 22c in which a reagent for differential white blood count (DIFF) is accommodated, and the like, and is able to supply reagents such as a staining reagent, a hemolytic agent, and a diluent, to the reaction chambers. The sample preparation unit 22 is also connected to the suction tube of the specimen suction unit 21, and is able to supply the blood specimen suctioned by the suction tube to the reaction chambers. The sample preparation unit 22 mixes the specimen with the reagent in each reaction chamber and stirs it to prepare a sample (measurement sample) for measurement by the detection unit 23.

The detection unit 23 is able to perform RBC (red blood cell) detection and PLT (platelet) detection by the sheath flow DC detection method. In the detection of RBC and PLT by the sheath flow DC detection method, a measurement sample obtained by mixing a specimen with a diluent is measured, and the information processing unit 5 performs processing for analyzing the measurement data obtained thereby to acquire numeric value data on RBC and PLT. Also, the detection unit 23 is configured to be able to perform HGB (hemoglobin) detection by the SLS-hemoglobin method, and to perform detection of WBC (white blood cell), NEUT (neutrophil), LYMPH (lymphocyte), EO (eosinophil), BASO (basophil), and MONO (monocyte), by the flow cytometry method using a semiconductor laser. For the five classes of white blood cells, a measurement sample obtained by mixing a specimen, a staining reagent for the five classes of white blood cells, a hemolytic agent, and a diluent is measured, and the information processing unit 5 performs processing for analyzing measurement data obtained thereby to acquire numeric value data on NEUT, LYMPH, EO, BASO, MONO, and WBC.

The aforementioned measurement items WBC, RBC, PLT, and HGB are included in a discrete item called a CBC item, and the measurement items WBC, RBC, PLT, HGB, NEUT, LYMPH, EO, BASO, and MONO are included in a discrete item called a CBC+DIFF item. Here, a "discrete item" refers to a group of measurement items for collectively designating multiple measurement items. In the present embodiment, both the measurement unit 2 and the measurement unit 3 are configured to be able to measure a specimen regarding the CBC item and the CBC+DIFF item.

The aforementioned detection unit 23 has a flow cell (not shown), and is configured to generate a liquid current in the flow cell by sending a measurement sample into the flow cell, irradiate blood cells contained in the liquid current passing through the inside of the flow cell with semiconductor laser light, and detect forward-scattered light, side-scattered light, and side fluorescence.

Light scattering is a phenomenon that occurs as a result of light changing its travelling direction due to particles such as blood cells that exist as obstacles in the travelling direction of the light. Information related to the size and material of particles can be obtained by detecting the scattered light. Specifically, information related to the size of particles (blood cells) can be obtained from forward-scattered light. Also, information regarding the inside of particles can be obtained from side-scattered light. When a blood cell particle is irradiated with laser light, side-scattered light intensity depends on complexity (shape, size, and density of a core, and amount of granules) of the cell interior. Accordingly, measurement of white blood cell classes and other measurement can be performed using this characteristic of the side-scattered light intensity.

When fluorescent material such as a stained blood cell is irradiated with light, it emits light having a longer wavelength than the wavelength of the irradiated light. The more stained a blood cell is, the higher the fluorescence intensity is, and information related to the degree of blood cell staining can be obtained by measuring this fluorescence intensity. Accordingly, measurement of white blood cell classes and other measurement can be performed using a difference in the (side-) fluorescence intensity.

The specimen container carrying unit 25 includes a hand unit 25a that is capable of holding the specimen container T, and the specimen container T accommodated in the specimen rack L is held by the hand unit 25a and pulled out of the specimen rack L due to the hand unit 25a being moved in the up-down direction and the forward-backward direction (Y direction). Also, the specimen container carrying unit 25 includes a specimen container setting unit 25b having a hole into which the specimen container T can be inserted. The specimen container T is set in this specimen container setting unit 25b, and is taken into the measurement unit 2 as a result of movement of the specimen container setting unit 25b.

The specimen container setting unit 25b can move to the position 21a of suction by the specimen suction unit 21. When the specimen container setting unit 25b has moved to the suction position, the specimen is suctioned by the specimen suction unit 21 from the set specimen container T.

Next, a configuration of the measurement unit 3 will be described. The model of the measurement unit 3 is different from the model of the measurement unit 2, and has a different configuration, as will be described later. The measurement unit 3 has a specimen suction unit 31, a sample preparation unit 32 for preparing a measurement sample to be used in the measurement of blood constituents such as blood cells, using blood suctioned by the specimen suction unit 31, and a detection unit 33 for detecting blood cells from the measurement sample prepared by the sample preparation unit 32. Also, the measurement unit 3 further has an intake 34 (see FIG. 2) for taking a specimen container T accommodated in a specimen rack L carried by the specimen carrying unit 4 into the measurement unit 3, and a specimen container carrying unit 35 for taking the specimen container T from the specimen rack L into the measurement unit 3 and carrying the specimen container T up to a position 31a of suction by the specimen suction unit 31. Since the configurations of the specimen suction unit 31, the sample preparation unit 32, the detection unit 33, the intake 34, and the specimen container carrying unit 35 are similar to the configurations of the specimen suction unit 21, the sample preparation unit 22, the detection unit 23, the intake 24, and the specimen container carrying unit 25, respectively, the description thereof will be omitted.

The measurement unit 3 is able to perform specimen measurement regarding the measurement items WBC, RBC, PLT, HGB, NEUT, LYMPH, EU, BASO, and MONO, which are the aforementioned CBC+DIFF item, similarly to the measurement unit 2.

In the measurement unit 3, a reagent container 32a is mounted which accommodates a reagent for reticulocyte (RET) measurement, in addition to reagent containers 22a, 22b, 22c, and so on that accommodate reagents for measurement regarding the measurement items WBC, RBC, PLT, HGB, NEUT, LYMPH, EO, BASO, and MONO, which are the aforementioned CBC+DIFF item that can be measured by the measurement unit 2. Thus, the measurement unit 3 is able to perform specimen measurement regarding the measurement item of RET, in addition to the CBC item and the DIFF item that can be measured by the measurement unit 2. In the measurement unit 3, RET measurement is performed by mixing the reagent for RET measurement with a specimen to prepare a measurement sample, and supplying the measurement sample to an optical detection unit for detection of WBC/DIFF (five white blood cell classes) in the detection unit 33.

<Configuration of Information Processing Unit>

Next, a configuration of the information processing unit 5 will be described. The information processing unit 5 can generate a specimen analysis result and display this analysis result by analyzing measurement data that is output from the measurement unit 2 or 3, creating a particle size distribution map such as a histogram of red blood cells or a scattergram of white blood cells, and performing blood cell count measurement for the sub-classes of white blood cells (NEUT, LYMPH, EO, BASO, and MONO). It is possible for the information processing unit 5 to be communicably connected to only one measurement unit 2, or to be communicably connected to the two measurement units 2 and 3.

Figure 4:
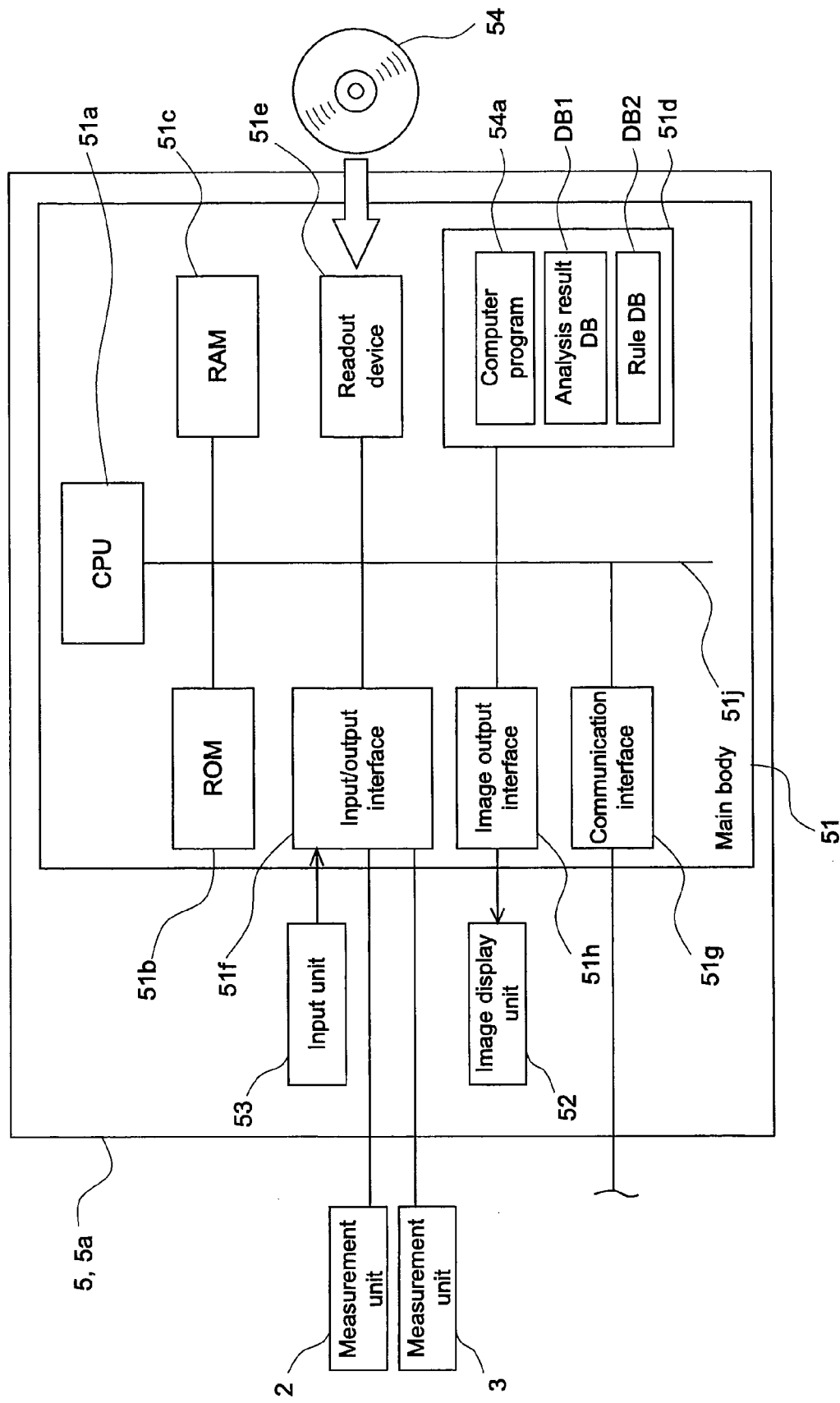
FIG. 4 is a block diagram showing a configuration of an information processing unit.

The information processing unit 5 is constituted by a computer. FIG. 4 is a block diagram showing a configuration of the information processing unit 5. The information processing unit 5 is realized by a computer 5a. As shown in FIG. 4, the computer 5a includes a main body 51, an image display unit 52, and an input unit 53. The main body 51 includes a CPU 51a, a ROM 51b, a RAM 51c, a hard disk 51d, a readout device 51e, an input/output interface 51f, a communication interface 51g, and an image output interface 51h. The CPU 51a, the ROM 51b, the RAM 51c, the hard disk 51d, the readout device 51e, the input/output interface 51f, the communication interface 51g, and the image output interface 51h are connected by a bus 51j.

The readout device 51e is able to read out a computer program 54a for causing the computer to function as the information processing unit 5 from a portable storage medium 54, and install the computer program 54a in the hard disk 51d.

The hard disk 51d is provided with an analysis result database DB1 for storing analysis results regarding the specimen measured by the connected measurement units 2 and 3, and a rule database DB2 for storing repeat rules, rerun rules, and reflex rules that are used to determine the necessity of remeasurement by the information processing unit 5, and host query rules used to determine whether or not the remeasurement necessity determination by the examination information management device 500 is necessary. The repeat rules, rerun rules, reflex rules, and host query rules will be described later in detail.

The input/output interface 51f is constituted, for example, by a serial interface conforming to USB, IEEE 1394, RS-232C, etc., a parallel interface conforming to SCSI, IDE, IEEE 1284, etc., an analog interface including a D/A converter, an A/D converter, etc., or the like. The input/output interface 51f is connected to the input unit 53, which includes a keyboard and a mouse, and data can be input to the computer 5a by a user using the input unit 53. Also, the input/output interface 51f can be connected to the measurement units and the specimen carrying unit 4 via communication cables. Thus, the information processing unit 5 is able to control the measurement units and the specimen carrying unit 4. Also, the input/output interface 51f can be connected to only one measurement unit. Further, the input/output interface can be simultaneously connected to the two measurement units 2 and 3 of different models, and can be simultaneously connected to two measurement units 2, 2 (or two measurement units 3, 3) of the same model. After the input/output interface 51f is thus connected to the measurement units and the specimen carrying unit 4, the connected measurement units and specimen carrying unit 4 can be controlled by the information processing unit 5.

<Configuration of Examination Information Management Device>

Figure 5:
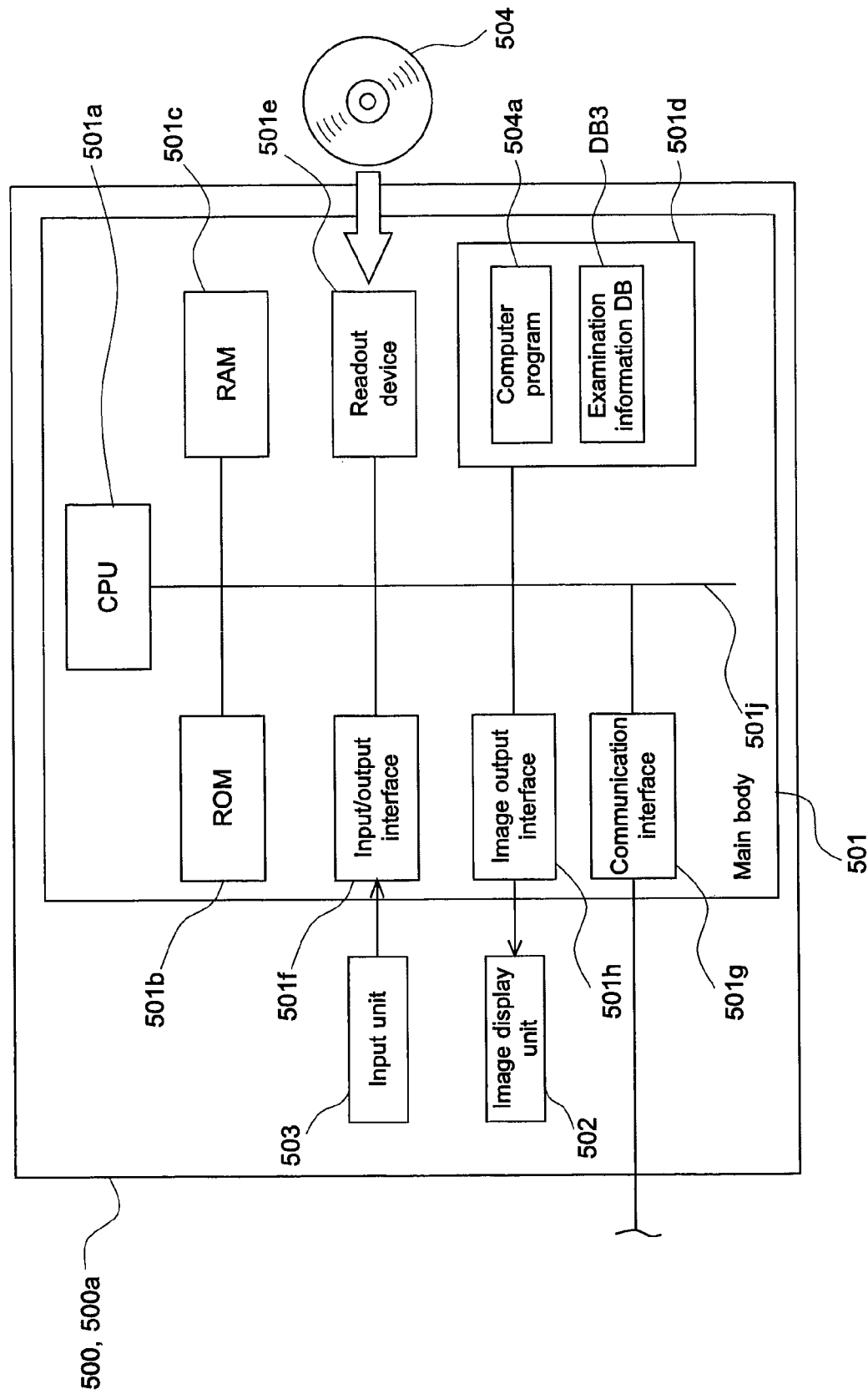
FIG. 5 is a block diagram showing a configuration of an examination information management device.

Next, a configuration of the examination information management device 500 will be described. The examination information management device 500 is constituted by a computer. FIG. 5 is a block diagram showing the configuration of the examination information management device 500. The examination information management device 500 is realized by a computer 500a. As shown in FIG. 5, the computer 500a includes a main body 501, an image display unit 502, and an input unit 503. The main body 501 includes a CPU 501a, a ROM 501b, a RAM 501c, a hard disk 501d, a readout device 501e, an input/output interface 501f, a communication interface 501g, and an image output interface 501h, and the CPU 501a, the ROM 501b, the RAM 501c, the hard disk 501d, the readout device 501e, the input/output interface 501f, the communication interface 501g, and the image output interface 501h are connected by a bus 501j.

The readout device 501e is able to read out a computer program 504a for causing a computer to function as the examination information management device 500 from a portable storage medium 504, and install the computer program 504a in the hard disk 501d.

The hard disk 501d is provided with an examination information database DB3 for storing examination information. The examination information database DB3 stores, as the examination information, patient information such as a patient ID and the name and age of a patient, a specimen measurement order, and analysis results and the like obtained by the specimen analyzers 100, 200, 300, and so on.

[Operation of Specimen Analysis System]

Next, operations of the specimen analysis system according to the present embodiment will be described.

<Specimen Measurement Operation>

Figure 6:
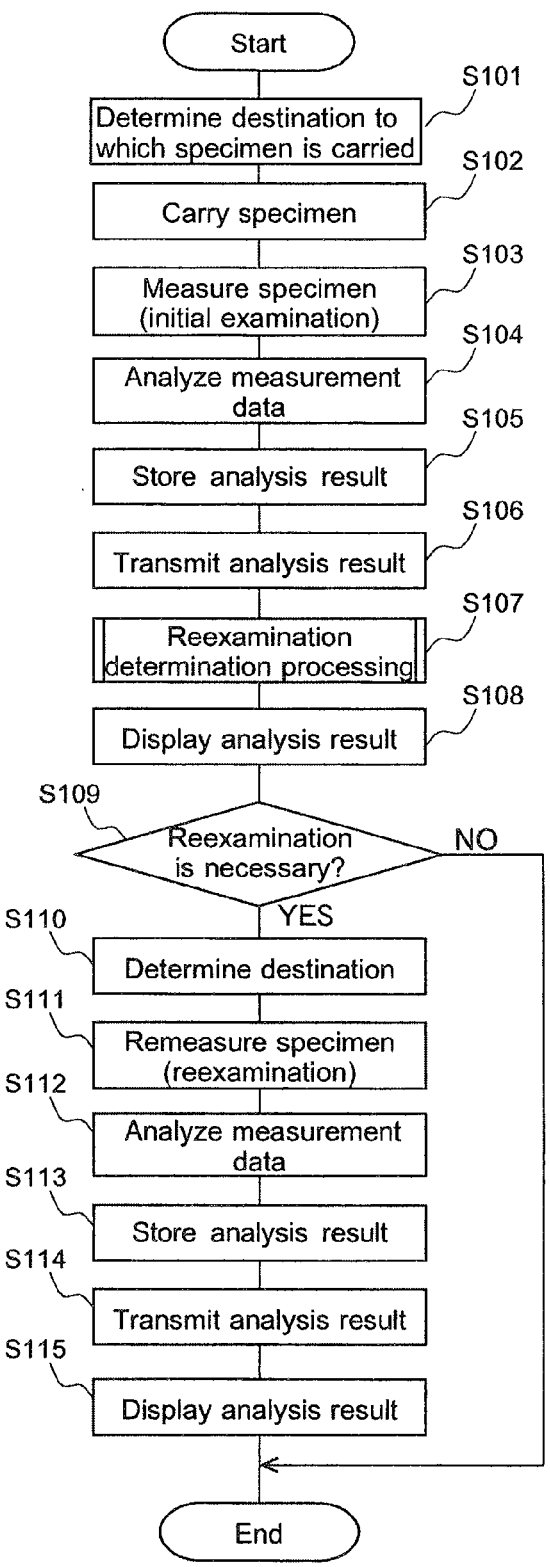
FIG. 6 is a flowchart showing a procedure of a specimen measurement operation.

First, a specimen measurement operation of the specimen analyzer according to the present embodiment will be described. FIG. 6 is a flowchart showing a procedure of a specimen measurement operation. Initially, an operator puts a specimen rack accommodating a specimen container on the specimen carrying unit 4 and gives the information processing unit 5 an instruction to start measurement, and the specimen rack thereby starts to be carried. A destination to which each specimen is carried is determined by the information processing unit 5 (step S101), and the specimen is carried by the specimen carrying unit 4 to the measurement unit that is the determined destination (step S102).

The destination of the specimen is determined based on a measurement order for this specimen. The measurement order is registered in advance in the examination information management device 500 or the information processing unit 5. A barcode indicating a specimen ID is printed on a specimen barcode label that is attached to each specimen container, and this barcode is read out by a barcode reader (not shown) mounted in the specimen carrying unit 4. The measurement order corresponding to the specimen ID that is read out from the barcode is found from the examination information management device 500 or the information processing unit 5, and the information processing unit 5 thereby acquires the measurement order. Measurement items are designated for which specimen measurement has been requested, in the measurement order. For example, in the case where only CBC and DIFF are designated in the measurement order, one of the measurement units 2 and 3 can be determined to be the destination because both of the measurement units 2 and 3 can measure the specimen regarding CBC and DIFF. Also, in the case where RET is designated in the measurement order, only the measurement unit 3 can be determined to be the destination because the measurement unit 2 cannot measure the specimen regarding RET.

The specimen container is carried to the destination that is determined as described above. By the information processing unit 5 controlling the measurement units, the measurement unit takes the specimen container inside, suctions the specimen from the specimen container, prepares a measurement sample for the measurement items designated in the measurement order, and measures the specimen (step S103). The measurement data that is obtained as a result thereof is given from the measurement unit to the information processing unit 5 and analyzed by the information processing unit, and a specimen analysis result is generated (step S104). Also, if an error occurs during the measurement of the specimen in step S103 and the measurement is not completed, error information indicating the error is given as measurement data to the information processing unit 5.

The above-described operation is performed for each specimen accommodated in the specimen rack, and the specimens are sequentially analyzed.

The CPU 51a registers the aforementioned analysis result in the analysis result database DB1 (step S105) and transmits the analysis result to the examination information management device 500 (step S106). Upon the analysis result being received by the examination information management device 500, the analysis result is registered in the examination information database DB3. Next, the CPU 51a executes reexamination determination processing (step S107).

Figure 7:
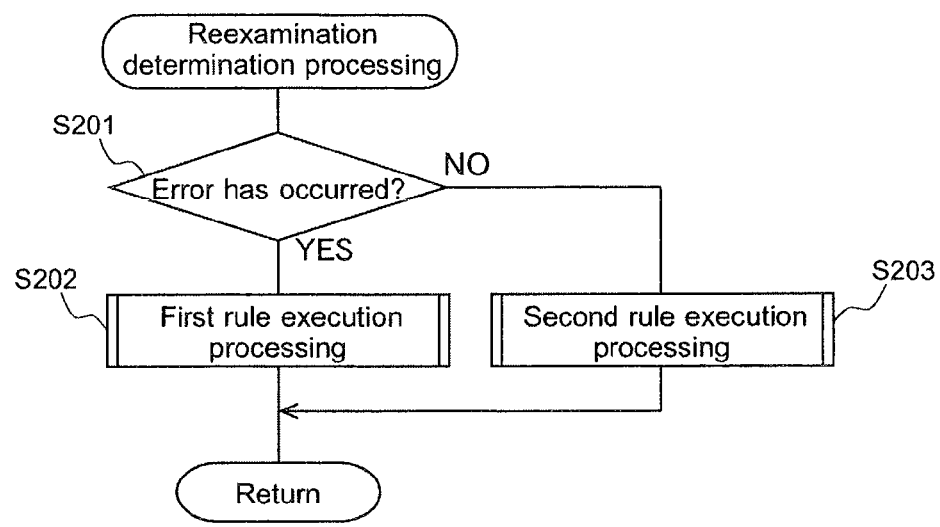
FIG. 7 is a flowchart showing a procedure of reexamination determination processing.

FIG. 7 is a flowchart showing a procedure of reexamination determination processing. Initially, the CPU 51a determines whether or not an error has occurred during the above-described specimen measurement (step S201). If the CPU 51a in the information processing unit 5 determines that a specimen measurement error has occurred (YES in step S201), it executes first rule execution processing for executing a repeat rule registered in the rule database DB2 (step S202). On the other hand, if it is determined in step S201 that a specimen measurement error has not occurred (NO in step S201), the CPU 51a executes second rule execution processing for executing a reflex rule, a rerun rule, or a host query rule that is registered in the rule database DB2 (step S203). After the first rule execution processing or the second rule execution processing is finished, the CPU 51a returns processing to a call address of the reexamination determination processing that is the main routine.

Figure 8:
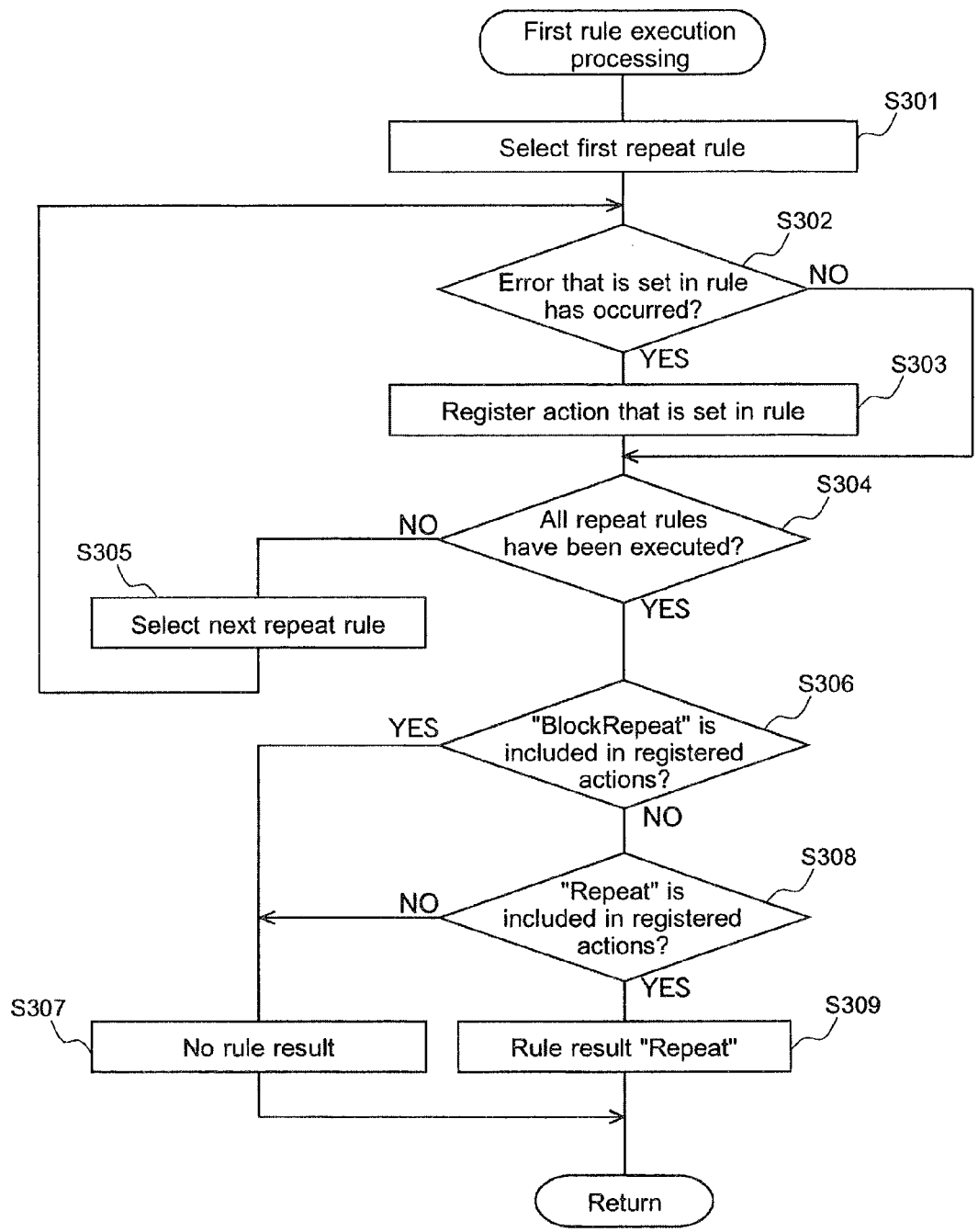
FIG. 8 is a flowchart showing a procedure of first rule execution processing.

Here, the first rule execution processing will be described in detail. FIG. 8 is a flowchart showing a procedure of the first rule execution processing. In the first rule execution processing, the CPU 51a initially selects the first repeat rule from among the repeat rules registered in the rule database DB2 (step S301).

Here, the repeat rules will be described. The repeat rules are rules for determining whether or not to perform a repeat test (remeasurement (reexamination) of a specimen regarding the same measurement items as those in specimen measurement (initial examination) by the same measurement unit as the measurement unit that performed the initial examination). Each repeat rule is described as an IF-THEN statement, and the IF part (condition part) indicates whether or not a predetermined specimen measurement error has occurred. In the THEN part, any of action commands "Repeat", "BlockRepeat", and "None" is set. The action command "Repeat" in the THEN part means "execute repeat test", and when "Repeat" is set in the THEN part of a rule, the repeat test is executed if the condition of the IF part of this rule is satisfied. "BlockRepeat" means "block repeat test execution". When "BlockRepeat" is set in the THEN part of a rule, the repeat test is not executed if the condition of the IF part of this rule is satisfied, regardless of the result of execution of other repeat rules (i.e., even if an instruction to "execute repeat test" is given as a result of execution of the other repeat rule). "None" means "not execute repeat test", and when "None" is set in the THEN part of a rule, an instruction to execute the repeat test is not given even if the condition of the IF part of the rule is satisfied. Here, even if the condition of the IF part of a repeat rule indicating "None" is satisfied, execution of the repeat test has priority when an instruction to "execute repeat test" is given as a result of execution of the other repeat rule. In other words, "BlockRepeat" and "None" have different priorities in the case of competing with a result of execution of the other rule. If the result "BlockRepeat" of execution of a rule competes with the result "Repeat" or "None" of execution of the other rule, "BlockRepeat" has priority and the repeat test is not executed. On the other hand, if the result "None" of execution of one rule competes with the result "Repeat" or "BlockRepeat" of execution of the other rule, "Repeat" or "BlockRepeat" has priority.

The following is a continuation of the description of the first rule execution processing based on FIG. 8. In step S302, the CPU 51a determines whether or not an error that is set in the IF part of the selected rule has occurred (step S302). If the error has not occurred (NO in step S302), the CPU 51a advances processing to step S304. On the other hand, if the error that is set in the IF part of the selected rule has occurred (YES in step S302), the CPU 51a registers the action ("Repeat", "BlockRepeat", or "None") that is set in the THEN part of the rule as an action planned to be executed in the RAM 51c (step S303), and advances processing to step S304.

In step S304, the CPU 51a determines whether or not all repeat rules registered in the rule database DB2 have been executed (step S304), and if any unexecuted repeat rule remains (NO in step S304), the CPU 51a selects the next repeat rule (step S305) and returns processing to step S302.

On the other hand, if, in step S304, all repeat rules registered in the rule database DB2 have been executed (YES in step S304), the CPU 51a determines whether or not "BlockRepeat" is included in the actions planned to be executed that are registered in the RAM 51c (step S306). If "BlockRepeat" is included in the actions planned to be executed (YES in step S306), the CPU 51a does not generate a rule result, which is a result of rule determination (step S307), and returns processing to a call address of the first rule execution processing in the reexamination determination processing.

If, in step S306, "BlockRepeat" is not included in the actions planned to be executed (NO in step S306), the CPU 51a determines whether or not "Repeat" is included in the registered actions planned to be executed (step S308). If "Repeat" is not included in the actions planned to be executed (NO in step S308), the CPU 51a does not generate a rule result, which is a result of rule determination (step S307), and returns processing to the call address of the first rule execution processing shown in FIG. 7.

On the other hand, if, in step S308, "Repeat" is included in the actions planned to be executed (YES in step S308), the CPU 51a generates a rule result "Repeat" (step S309). This rule result is information added to the specimen analysis result, and is displayed on an analysis result output screen. The analysis result display screen will be described later. After finishing the process in step S309, the CPU 51a returns processing to the call address of the first rule execution processing shown in FIG. 7.

Figure 9A:
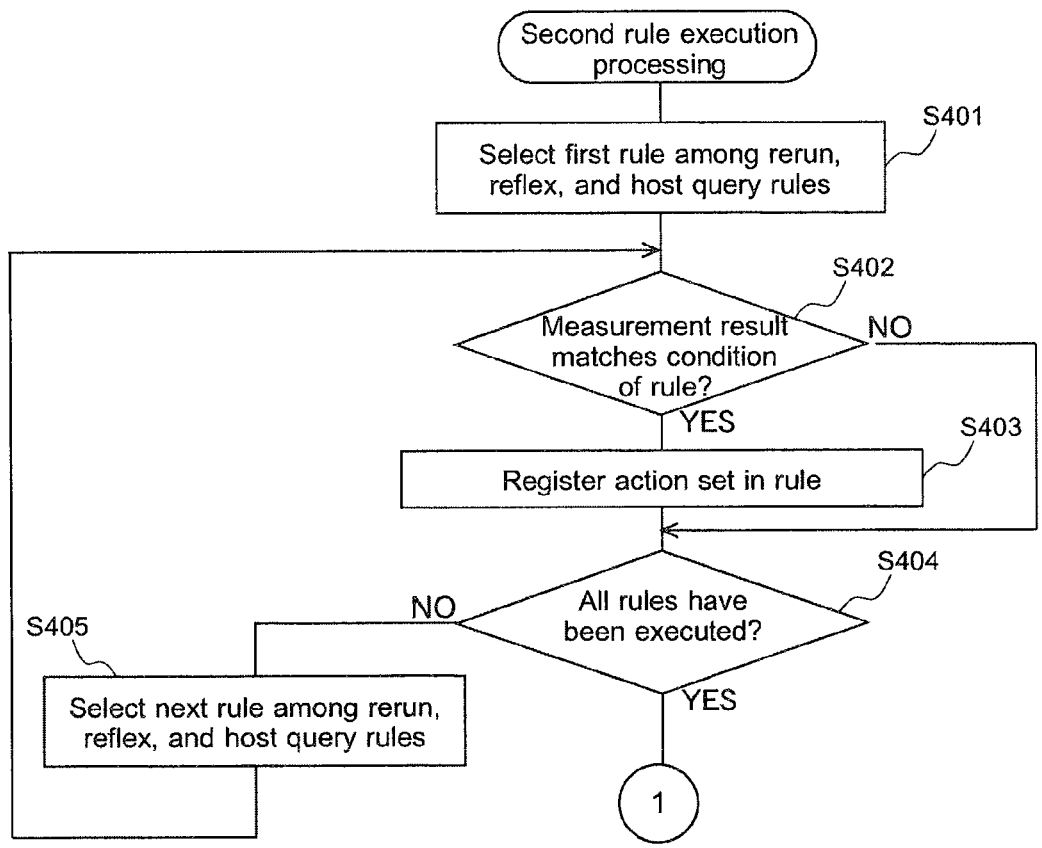
FIG. 9A is a flowchart showing the first half of a procedure of second rule execution processing.
Figure 9B:
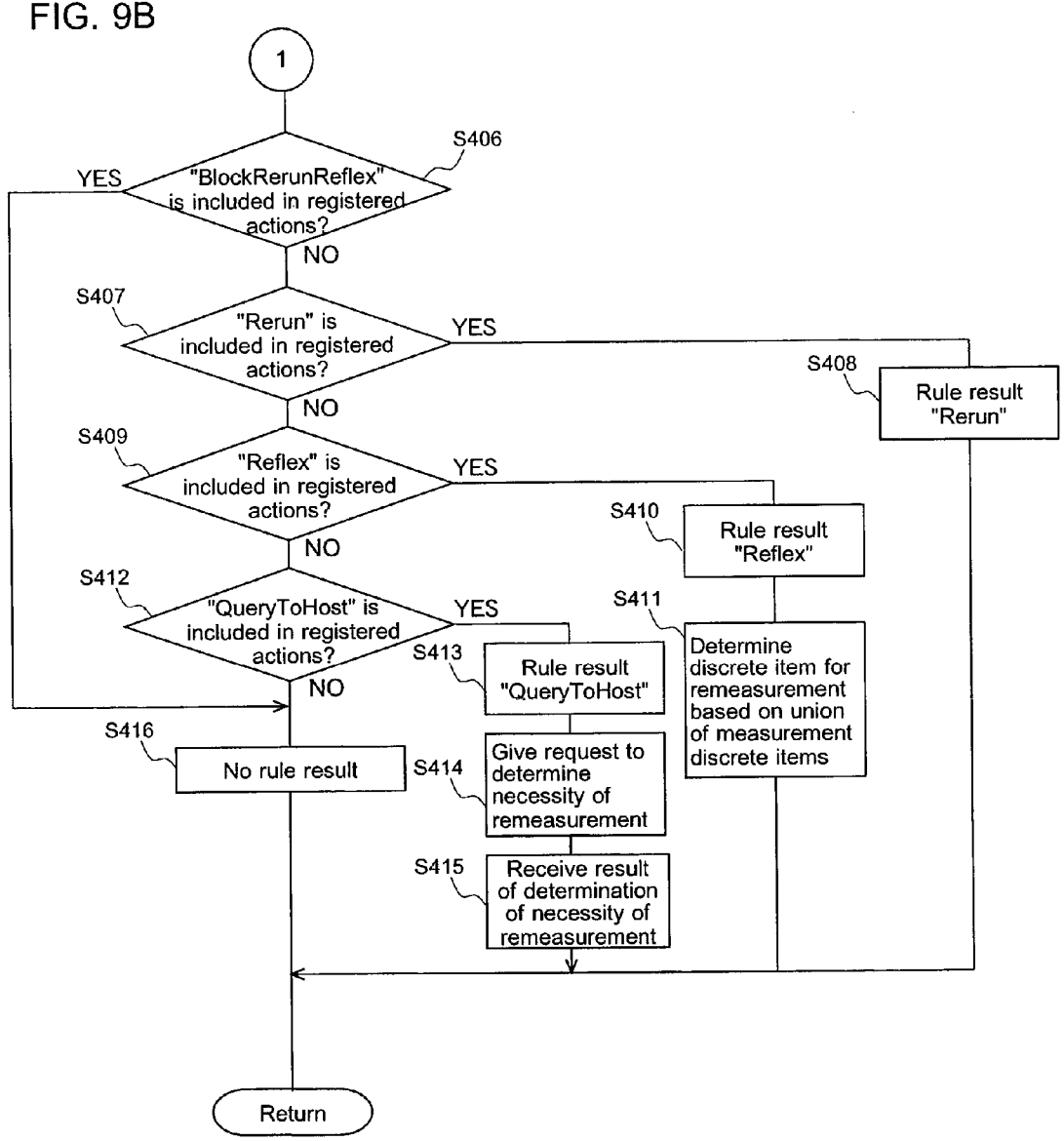
FIG. 9B is a flowchart showing the latter half of a procedure of second rule execution processing.

Next, the second rule execution processing will be described in detail. FIGS. 9A and 9B are flowcharts showing a procedure of the second rule execution processing. In the second rule execution processing, the CPU 51a initially selects the first rule from among reflex rules, rerun rules, and host query rules that are registered in the rule database DB2 (step S401).

Here, the reflex rules, the rerun rules, and the host query rules will be described. The reflex rules are rules for determining whether or not to perform a reflex test (reexamination operation in which a specimen is remeasured regarding reexamination items that include a measurement item that is different from the measurement items for which the specimen was measured in the initial examination). The rerun rules are rules for determining whether or not to perform a rerun test (reexamination operation of remeasuring a specimen regarding the same measurement items as those in the initial examination by a measurement unit that is the same as, or different from, the measurement unit that performed the initial examination). The rerun test is performed in the case where, for example, it is presumed that an abnormality in a measured value of a specimen derives from a device failure, that an abnormality in a measured value of a specimen derives from mismanagement at the time of specimen collection, or the like. Each of the reflex rules and the rerun rules is described as an IF-THEN statement, and the IF part (condition part) thereof is set as a conditional expression related to a numeric value of an analysis result. In the THEN part of each reflex rule, an action command is set that contains designation of reexamination items (a discrete item for which remeasurement is performed), such as "Reflex (DIFF)", "Reflex (DIFF+RET)", or "Reflex (RET)". Meanwhile, in the THEN part of each rerun rule, an action command is set that contains designation of a measurement unit for performing remeasurement, such as "Rerun (SameModule)", "Rerun (DifferentModule)", or "Rerun (AnyModule)". "Rerun (SameModule)" is an action command for giving an instruction to execute remeasurement regarding the same items as those in the initial examination by the same measurement unit as the measurement unit that performed measurement in the initial examination, "Rerun (DifferentModule)" is an action command for giving an instruction to execute remeasurement regarding the same items as those in the initial examination by a measurement unit other than the measurement unit that performed measurement in the initial examination, and "Rerun (AnyModule)" is an action command for giving an instruction to execute remeasurement regarding the same items as those in the initial examination by a measurement unit that is the same as, or different from, the measurement unit that performed measurement in the initial examination.

For example, in the case where a reflex rule "IF WBC>100 THEN Reflex (DIFF)" is set, an instruction to execute the reflex test regarding the DIFF item is given if the measurement result for WBC is larger than 100. In this case, the measurement unit that is able to perform specimen measurement regarding the DIFF item, that is, either of the measurement units 2 and 3 is determined to be the destination. Also, for example, in the case where a rerun rule "IF RBC<30 THEN Rerun (SameModule)" is set, an instruction to execute the rerun test regarding the same item as in the initial examination (in this case, the CBC item including RBC) by the same measurement unit as the measurement unit that performed the initial examination is given if the measurement result regarding RBC is smaller than 30. In this case, if the initial examination was performed by the measurement unit 2, the measurement unit 2 is determined to be the destination.

Among these action commands for the rerun test and the action commands for the reflex test, execution of the action commands for the rerun test has a higher priority. In other words, in the case where an instruction to execute the rerun test is given as a result of execution of one rule, and an instruction to execute the reflex test is given as a result of execution of the other rule, execution of the rerun test has priority and the reflex test is not executed. Furthermore, in the case where a plurality of action commands for the reflex test compete with each other (in the case where a plurality of reflex rules are satisfied), an instruction to perform measurement regarding all measurement items (discrete item) designated in these action commands is given. For example, in the case where an instruction indicating an action command "Reflex (DIFF)" is given as a result of execution of one reflex rule and an instruction indicating an action command "Reflex (RET)" is given as a result of execution of the other reflex rule, reexamination of the specimen is executed regarding both "DIFF" and "RET". Thus, in the case where a plurality of action commands for the reflex test compete with each other, remeasurement of the specimen is performed regarding a union of the measurement items designated in these action commands.

Also, in the case where the reflex test is executed, remeasurement of the specimen is performed not only regarding the measurement items (discrete item) designated in the action command for the reflex test, but also regarding the measurement items (discrete item) regarding which measurement was performed in the initial examination. The information processing unit 5 compares the analysis result regarding the measurement items that are added in the reflex test with the analysis result of reexamination regarding the same measurement items as those in the initial examination, and determines whether or not the analysis result is reliable. In other words, reexamination is performed not only regarding the measurement items designated in the action command for the reflex test but also regarding the measurement items regarding which measurement was performed in the initial examination, and it is thereby possible to determine whether or not the analysis result of reexamination is reliable.

"Host query" is an operation of giving the examination information management device 500 a request to determine the necessity of remeasurement of the specimen using the examination information held by the examination information management device 500, in the case where it cannot be determined whether or not to remeasure the specimen, using only the analysis result generated in the specimen analyzer 100. Each host query rule is described as an IF-THEN statement, and the IF part (condition part) thereof is set as a conditional expression related to a numeric value of an analysis result. In the THEN part of the host query rule, an action command "QueryToHost" for giving an instruction to perform "host query" is set.

The host query action command has a lower priority than action commands for the rerun test and the reflex test. In other words, in the case where an instruction to execute the rerun test or the reflex test is given as a result of execution of a rerun rule or a reflex rule, execution of the rerun test or the reflex test has priority, and host query is not executed even if an instruction to execute host query is given as a result of execution of a host query rule.

Also, in the THEN part of the reflex rules, rerun rules, and host query rules, an action command "BlockRerunReflex" or "None" can be set. "BlockRerunReflex" means "block execution of rerun test, reflex test, and host query". When "BlockRerunReflex" is set in the THEN part of a rule, the rerun test, the reflex test, and the host query are not executed if the condition of the IF part of this rule is satisfied, regardless of the result of execution of the other rule (i.e., even if an instruction to "execute rerun test, reflex test, or host query" is given as a result of execution of the other rule). Also, "None" means "not execute rerun, reflex, and host query", and when "None" is set in the THEN part of a rule, an instruction to execute the rerun test, the reflex test, or the host query is not given if the condition of the IF part of this rule is satisfied. Here, even if the condition of the IF part of a rule indicating "None" is satisfied, execution of the rerun test, the reflex test, or the host query has priority when an instruction to "execute rerun test, reflex test, or host query" is given as a result of execution of the other rerun rule, reflex rule, or host query rule. In other words, "BlockRerunReflex" and "None" have different priorities in the case of competing with a result of execution of the other rule. In the case where a result "BlockRerunReflex" of execution of one rule competes with a result "Reflex", "Rerun", "QueryToHost", or "None" of execution of the other rule, "BlockRerunReflex" has priority, and the reflex test, the rerun test, and the host query are not executed. On the other hand, in the case where a result "None" of execution of one rule competes with a result "Reflex", "Rerun", "QueryToHost", or "BlockRerunReflex" of execution of the other rule, "Reflex", "Rerun", "QueryToHost", or "BlockRerunReflex" has priority.

The following is a continuation of the description of the second rule execution processing based on FIG. 9. In step S402, the CPU 51a determines whether or not the analysis result generated in step S104 matches the condition set in the IF part of the selected rule (step S402). If the analysis result does not match the condition (NO in step S402), the CPU 51a advances processing to step S404. On the other hand, if the analysis result matches the condition (YES in step S402), the CPU 51a registers the action set in the THEN part of the rule as an action planned to be executed in the RAM 51c (step S403), and advances processing to step S404.

In step S404, the CPU 51a determines whether or not all rerun rules, reflex rules, and host query rules that are registered in the rule database DB2 have been executed (step S404), and if any unexecuted rule remains (NO in step S404), the CPU 51a selects the next rule (step S405) and returns processing to step S402.

On the other hand, if, in step S404, all rerun rules, reflex rules, and host query rules that are registered in the rule database DB2 have been executed (YES in step S404), the CPU 51a determines whether or not "BlockRerunReflex" is included in the actions planned to be executed that are registered in the RAM 51c (step S406). If "BlockRerunRe-flex" is included in the actions planned to be executed (YES in step S406), the CPU 51a does not generate a rule result, which is a result of rule determination (step S416), and returns processing to a call address of the second rule execution processing shown in FIG. 7.

If, in step S406, "BlockRerunReflex" is not included in the actions planned to be executed (NO in step S406), the CPU 51a determines whether or not "Rerun" is included in the registered actions planned to be executed (step S407). If "Rerun" is included in the actions planned to be executed (YES in step S407), the CPU 51a generates a rule result "Rerun", which is a result of rule determination (step S408), and returns processing to the call address of the second rule execution processing shown in FIG. 7.

If, in step S407, "Rerun" is not included in the actions planned to be executed (NO in step S407), the CPU 51a determines whether or not "Reflex" is included in the registered actions planned to be executed (step S409). If "Reflex" is included in the actions planned to be executed (YES in step S409), the CPU 51a generates a rule result "Reflex", which is a result of rule determination (step S410), and determines a discrete item to be a subject of remeasurement (step S411). If, in step S411, the conditions of the IF parts of a plurality of reflex rules are matched, a union of the discrete items designated in the action commands in these reflex rules are determined to be the subjects of remeasurement, as mentioned above. After finishing the aforementioned process in step S411, the CPU 51a returns processing to the call address of the second rule execution processing shown in FIG. 7.

If, in step S409, "Reflex" is not included in the actions planned to be executed (NO in step S409), the CPU 51a determines whether or not "QueryToHost" is included in the registered actions planned to be executed (step S412). If "QueryToHost" is included in the actions planned to be executed (YES in step S412), the CPU 51a generates a rule result "QueryToHost", which is a result of rule determination (step S413), and gives the examination information management device 500 a request to determine the necessity of remeasurement, via a communication network (step S414). In accordance with this request, the examination information management device 500 determines the necessity of remeasurement of the specimen, based on the examination information. The details of this necessity determination processing will be described later. The examination information management device 500, upon completing the determination of the necessity of remeasurement, transmits the result of the necessity determination to the information processing unit 5. The CPU 51a in the information processing unit 5 receives the result of the determination of the necessity of remeasurement from the examination information management device 500 (step S415), and returns processing to the call address of the second rule execution processing shown in FIG. 7.

If, in step S412, "QueryToHost" is not included in the actions planned to be executed (NO in step S412), the CPU 51a does not generate a rule result, which is a result of rule determination (step S416), and returns processing to the call address of the second rule execution processing shown in FIG. 7.

Figure 10:
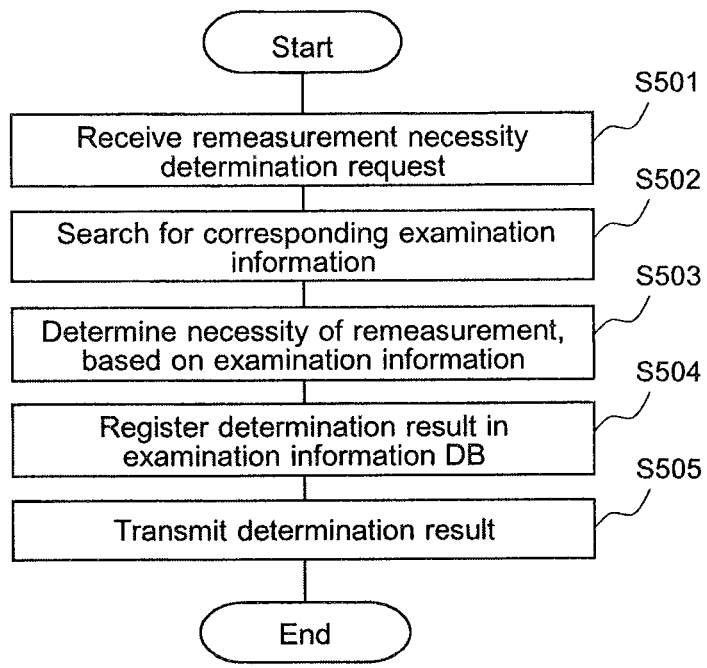
FIG. 10 is a flowchart showing a procedure of reexamination determination processing by the examination information management device.

Next, the reexamination determination processing by the examination information management device 500 will be described. FIG. 10 is a flowchart showing a procedure of the reexamination determination processing by the examination information management device 500. The CPU 501a in the examination information management device 500 receives data of the request to determine the necessity of remeasurement of the specimen that is transmitted from the information processing unit 5 (step S501). This request data contains the specimen ID of the specimen that is the subject of the determination of the necessity of remeasurement. The CPU 501a searches the examination information database DB3 for the examination information regarding the specimen that is the subject of the determination of the necessity of remeasurement, using the specimen ID (step S502).

Upon obtaining the examination information, the CPU 501a determines the necessity of remeasurement, based on the examination information (step S503). In this processing, the necessity of remeasurement is determined using information that is held in the information processing unit 5 that is not the analysis result. For example, the CPU 501a compares the analysis result at this time (hereinafter referred to as a "current value") with the analysis result at the previous time (hereinafter referred to as a "previous value") regarding a specific measurement item. If, as a result, the current value diverges from the previous value by a reference value or more, the current value is not reliable, and the CPU 501a therefore determines that remeasurement is necessary regarding the same discrete item as that of the analysis result at this time. Here, the past analysis results including the previous value are information that is not held in the information processing unit 5. Also, for example, the CPU 501a can determine whether or not remeasurement of the specimen is necessary by determining whether or not the analysis result at this time obtained by the specimen analyzer 100 and the analysis results obtained by the other specimen analyzers 200, 300, and so on satisfy a predetermined relationship. Here, the analysis results obtained by the specimen analyzers 200, 300, and so on are information that is not held by the information processing unit 5 in the specimen analyzer 100.

Upon completion of the above-described determination of the necessity of remeasurement, the CPU 501a registers the determination result in the examination information database DB3 (step S504), transmits this determination result to the information processing unit 5 (step S505), and ends processing. The result of the determination of the necessity of remeasurement transmitted from the examination information management device 500 is received by the information processing unit 5 in step S415, which was described above.

The following is a continuation of the description of the specimen measurement operation based on FIG. 6. Upon completion of the above-described reexamination determination processing, the CPU 51a causes the image display unit 52 to display the analysis result generated in step S104 (step S108). Next, the CPU 51a determines whether or not it has been determined that remeasurement of the specimen is necessary in the above-described first rule execution processing or second rule execution processing (step S109), and if it has been determined that remeasurement is necessary (YES in step S109), the CPU 51a determines the destination to which the specimen is carried (step S110). If, in the process in step S110, remeasurement indicated by the instruction is the repeat test, the measurement unit that executed the initial examination is determined to be the destination of the specimen. Also, if an instruction indicating "Rerun (SameModule)" is given, the measurement unit that executed the initial examination is determined to be the destination of the specimen, and if an instruction indicating "Rerun (DifferentModule)" is given, a measurement unit other than the measurement unit that executed the initial examination is determined to be the destination of the specimen. If an instruction indicating "Rerun (AnyModule)" is given, the measurement unit to be the destination is determined in accordance with operation states of the measurement units 2 and 3 (e.g., a measurement unit that is not executing measurement is determined to be the destination). If an instruction indicating the reflex test is given, a measurement unit that can execute the designated discrete item is determined to be the destination.

Upon the destination of the specimen being determined, the CPU 51a controls the specimen carrying unit 4 so as to carry the specimen to this destination, and remeasures the specimen by controlling the measurement unit (step S111). Remeasurement data is given to the information processing unit 5, and the CPU 51a in the information processing unit 5 analyzes the remeasurement data and generates an analysis result (remeasurement result) (step S112). Further, the CPU 51a registers the obtained analysis result in the analysis result database DB1 (step S113) and transmits the analysis result to the examination information management device 500 (step S114). Upon the analyzer being received by the examination information management device 500, the analyzer is registered in the examination information database DB3. Further, the CPU 51a causes the image display unit 52 to display the analysis result generated in step S112 (step S115) and ends processing.

On the other hand, if it is not determined in step S109 that remeasurement is necessary (NO in step S109), the CPU 51a does not remeasure the specimen and ends processing.

<Rule Setting Processing>

Next, rule setting processing by the information processing unit 5 will be described. The rule setting processing is processing by which a user sets desired repeat rules, reflex rules, rerun rules, and host query rules.

Figure 11:
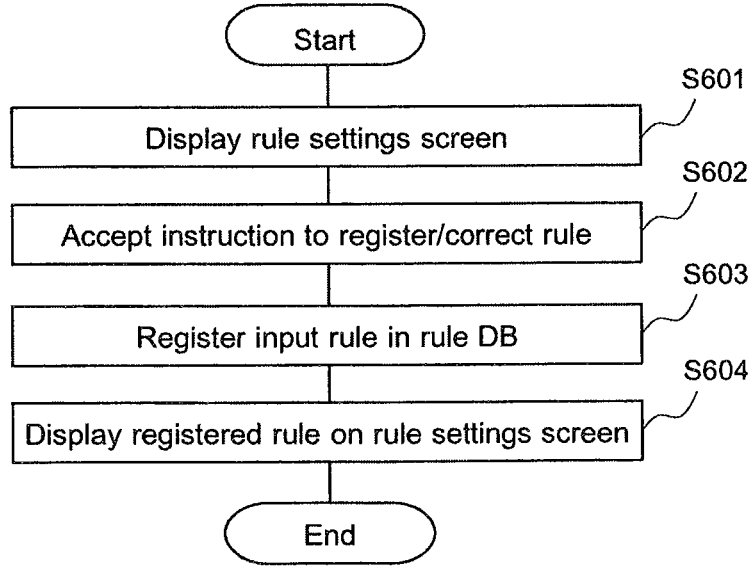
FIG. 11 is a flowchart showing a procedure of rule setting processing.
Figure 12:
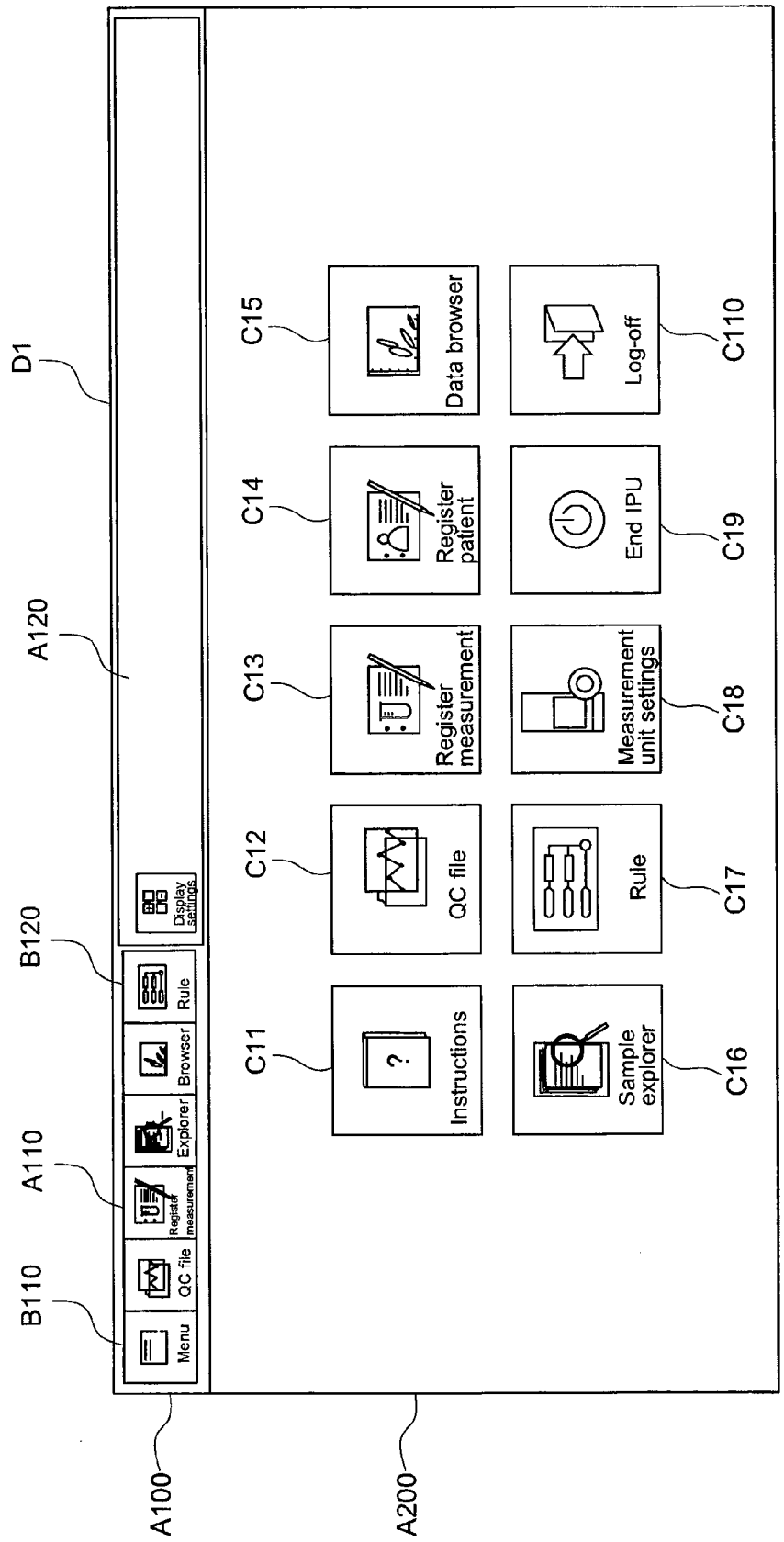
FIG. 12 is a diagram showing a menu screen of the information processing unit.

FIG. 11 is a flowchart showing a procedure of the rule setting processing. A menu screen is displayed on the image display unit 52 immediately after the information processing unit 5 is activated. FIG. 12 is a diagram showing the menu screen of the information processing unit 5. The menu screen D1 can be transitioned to other screens such as a rule settings screen, which will be described later.

As shown in FIG. 12, the menu screen D1 is provided with a toolbar region A100 in which a toolbar is displayed and a main region A200 in which a plurality of icons for transitioning to other screens are displayed. The toolbar region A100 and the main region A200 are provided not only in the menu screen D1 but also in other screens of the information processing unit. Also, the toolbar region A100 is divided into a left region and a right region. The left region is a fixed button region A110 in which common buttons are displayed in any screen, and the right region is a variable button region A120 in which displayed buttons are different for each screen. In the fixed button region A110, a "menu" button B110 for displaying the menu screen, a "rule" button B120 for displaying the rule settings screen, as well as a plurality of buttons for displaying other screens are displayed. On the other hand, in the variable button region A120 in the menu screen D1, a "display settings" button for setting a display mode of the menu screen D1 is displayed.

Note that the "icon" mentioned here refers to an image that is assigned a specific function and is designed to symbolically represent this function, and images displayed within a window are included therein.

The toolbar region A100 is provided in the uppermost part of the screen. The main region A200 is provided below the toolbar region A100. The main region A200 is a region having a larger area than the toolbar area A100, and major contents of this screen are displayed therein. The main region A200 of the menu screen D1 is provided with an "instructions" icon C11 for displaying instructions, a "QC file" icon C12 for displaying an accuracy management screen, a "measurement registration" icon C13 for displaying a measurement order registration screen, a "patient registration" icon C14 for displaying a patient information registration screen, a "data browser" icon C15 for displaying a measurement result details screen, a "sample explorer" icon C16 for displaying a measurement result list screen, a "rule" icon C17 for displaying the rule settings screen, a "measurement unit settings" icon C18 for displaying a measurement unit settings screen that is used to set the measurement units, an "end IPU" icon C19 for shutting down the information processing unit 5, and a "log-off" icon C110 by which the user logs off the information processing unit 54. The icons C11 to C18 are assigned functions of switching display from the menu screen D1 to the other screen, and when any of the icons C11 to C18 is selected by a mouse click operation, display is switched to a corresponding screen. Also, the button B120 is assigned the same function as the icon C17, and when the button B120 or the icon C17 is selected, a command to give an instruction to display the rule settings screen is issued by the CPU 51a, and the rule settings screen is displayed in accordance with this command.

The CPU 51a determines whether or not it has accepted an instruction to switch display to the rule settings screen. As mentioned above, an operator can give the information processing unit 5 the instruction to switch display to the rule settings screen by an operation of selecting the icon C17 displayed in the main region A200 or the button B120 displayed in the toolbar region A100 in the menu screen D1. The CPU 51a, upon accepting the instruction to switch display to the rule settings screen, executes the rule setting processing, and causes the image display unit 52 to display the rule settings screen (step S601).

Figure 13:
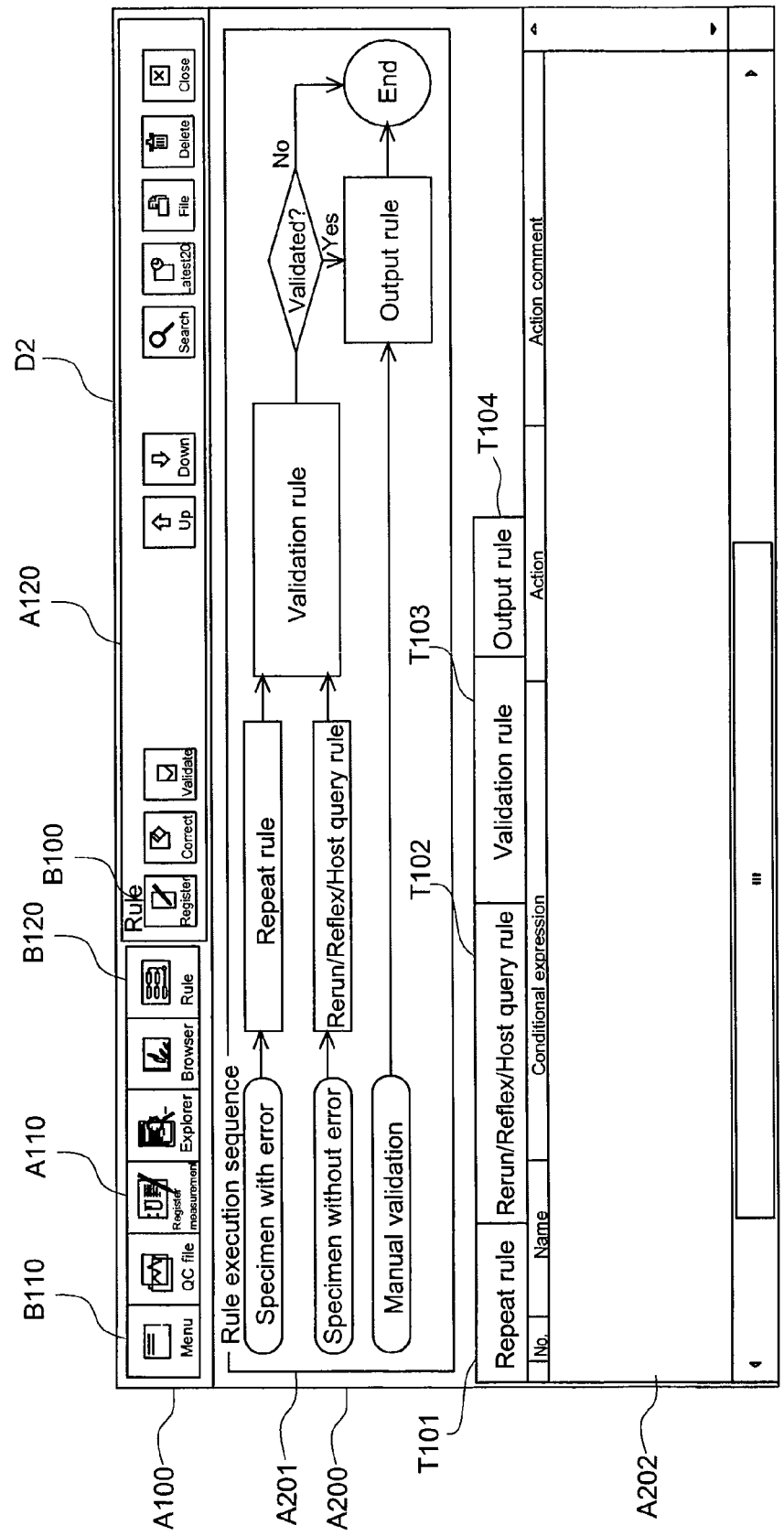
FIG. 13 is a diagram showing an example of a rule settings screen.

FIG. 13 is a diagram showing an example of the rule settings screen. The rule settings screen D2 is provided with a toolbar region A100 and a main region A200, similarly to the other screens. Since the content displayed in a fixed button region A110 in the toolbar region A100 is similar to that in the above-described menu screen D1, the description thereof will be omitted.

The main region A200 of the rule settings screen D2 is provided with an upper region A201 for displaying a diagram (flowchart) illustrating a rule execution sequence, and a lower region A202 for displaying a list of set rules. The upper end of the lower region A202 is provided with a "Repeat rule" tab T101, a "Rerun/Reflex/Host Query rule" tab T102, a "validation rule" tab T103, and an "output rule" tab T104. Each of the tabs T101 to T104 can be selected. In a state where the tab T101 is selected, a list of currently registered repeat rules is displayed in the lower region A202; in a state where the tab T102 is selected, a list of currently registered rerun rules, reflex rules, and host query rules is displayed in the lower region A202; in a state where the tab T103 is selected, a list of currently registered validation rules is displayed in the lower region A202; and in a state where the tab T104 is selected, a list of currently registered output rules is displayed in the lower region A202.

Figure 14:
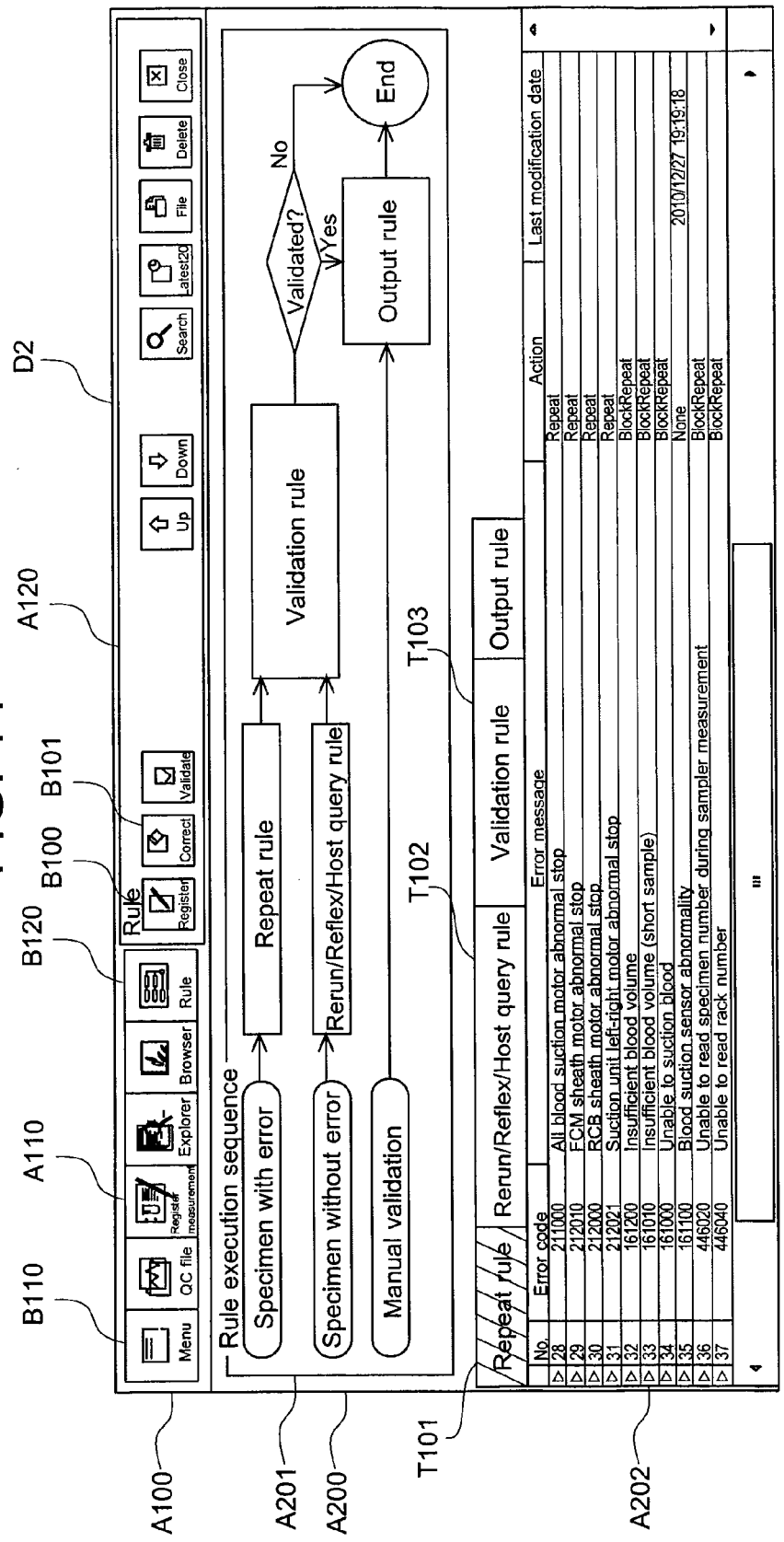
FIG. 14 is a diagram showing an example of the rule settings screen in a state where a list of repeat rules is displayed.

FIG. 14 is a diagram showing an example of the rule settings screen in a state where a list of repeat rules is displayed. As shown in FIG. 14, if the tab T101 is selected, a list of the repeat rules registered in the rule database DB2 is displayed in the lower region A202. In the lower region A202, each line displays information (rule number, error code, error message, action, updated date) indicating one repeat rule. Each line in the lower region A202 can be selected by a mouse click operation or the like.

Figure 15:
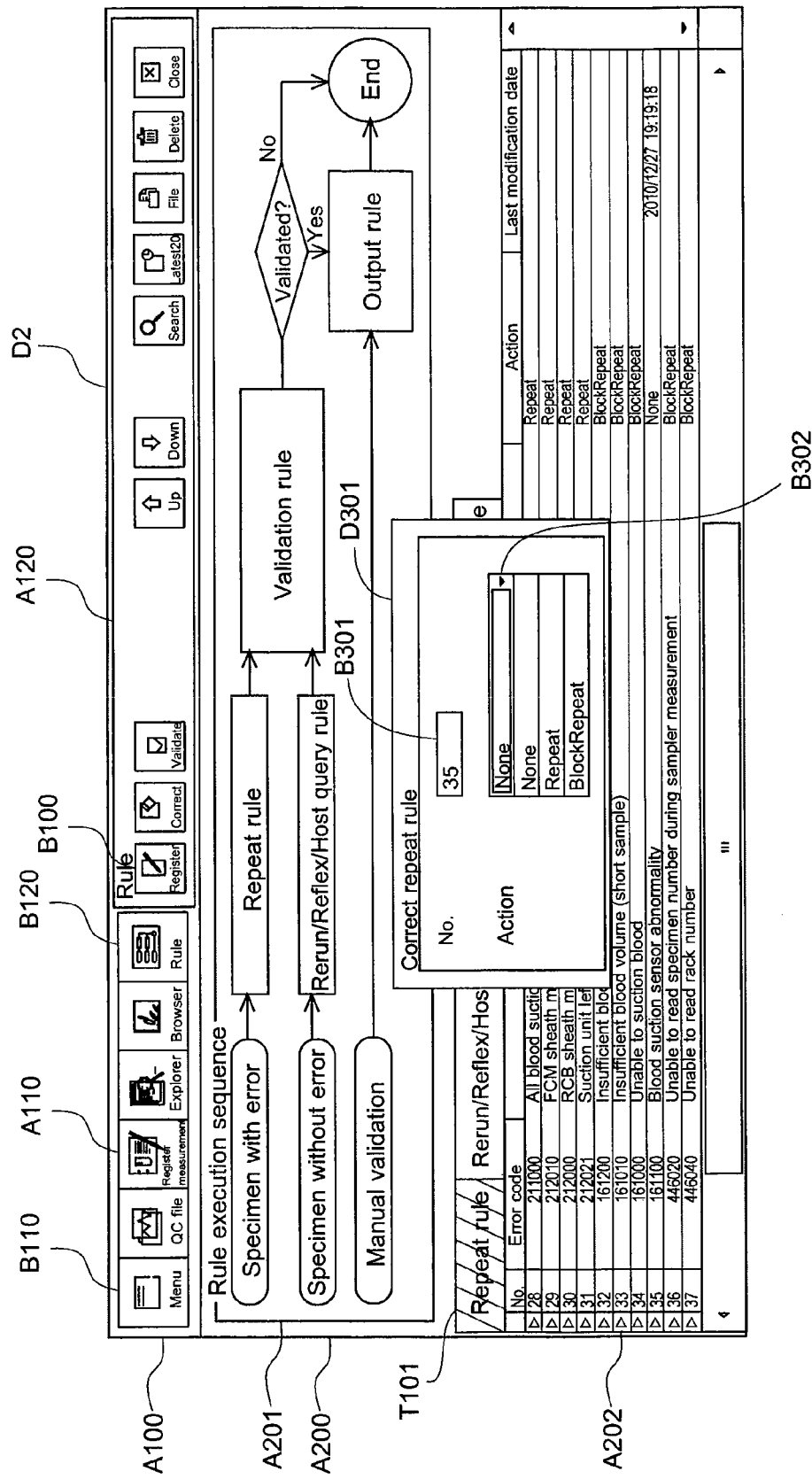
FIG. 15 is a diagram showing a repeat rule correction dialog.

Also, the variable button region A120 in the rule settings screen D2 is provided with a "register" button B100 for registering a rule and a "correct" button B101 for correcting a rule. When correcting a repeat rule, the user operates the input unit 53 and selects the "correct" button B101 in a state of selecting the repeat rule to be corrected that is displayed in the lower region A202. Thus, a repeat rule correction dialog is displayed. FIG. 15 is a diagram showing the repeat rule correction dialog. The repeat rule correction dialog D301 is provided with a region B301 in which the number of the repeat rule to be corrected is displayed, and a button B302 for selecting an action command. Upon the button B302 being selected, a drop-down list is displayed in which three action commands that can be set, namely "None", "Repeat", and "BlockRepeat" are listed. The user operates the input unit 53 and selects the button B302 to display the drop-down list, and selects one of the listed action commands displayed in the drop-down list. Thus, the repeat rule can be corrected.

Figure 16:
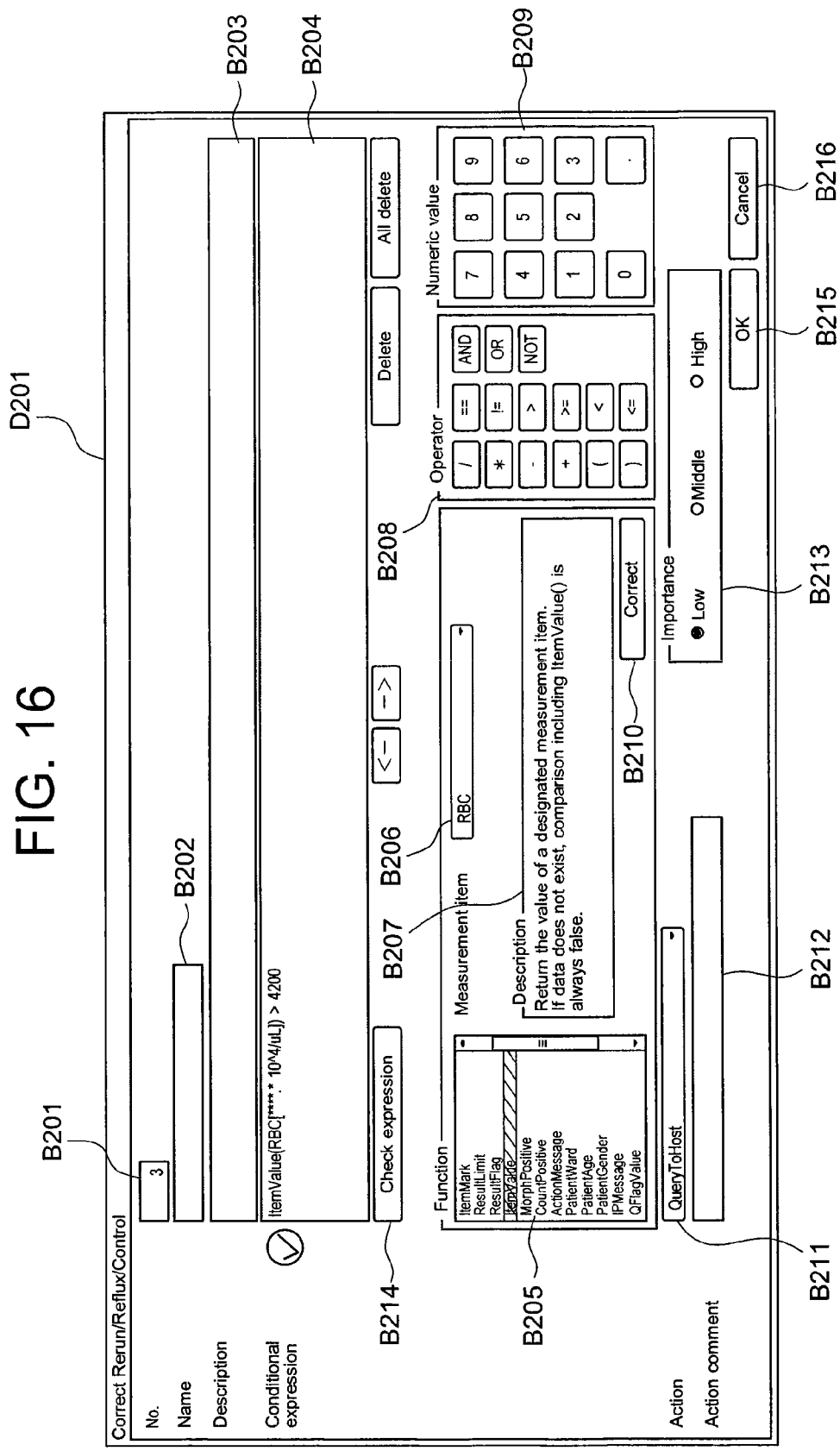
FIG. 16 is a diagram showing a rule registration dialog.

In the case of adding a new rerun rule, reflex rule, or host query rule, the user operates the input unit 53 and selects the "register" button B100 in a state where the tab T102 is selected and the list of rerun rules, reflex rules, and host query rules is displayed in the lower region A202. The CPU 51a, upon accepting selection of the button B100, displays a rule registration dialog so as to be superposed on the rule settings screen D2. FIG. 16 is a diagram showing the rule registration dialog. The rule registration dialog D201 is a screen for setting reflex rules, rerun rules, and host query rules. The rule registration dialog D201 is provided with a display region B201 in which a rule number is displayed, an input box B202 in which a rule name is input, an input box B203 in which a description of the rule is input, and a display region B204 for displaying an input conditional expression. The input boxes B202 and B203 are edit controls, in which text can be input from the keyboard of the input unit 53, and the input text is displayed therein. In the display region B201, a rule number is displayed. The rule number is a number automatically assigned by the information processing unit 5, and each registered rule is assigned an individual rule number. Also, in the display region B204, a conditional expression, which is input as described below, is displayed.

Below the display region B204, a tool for inputting a conditional expression (IF part) is displayed. Specifically, a selection region B205 for designating a function of the conditional expression is displayed. In the selection region B205, a list of function names that can be used as the conditional expression is displayed, and each function name can be selected. The user selects a function to be used as the conditional expression from among the function names displayed in the selection region B205, using the input unit 53. In the example shown in FIG. 16, a function "ItemValue" is selected.

On the right of the selection region B205, a button B206 for displaying a drop-down list (pull-down menu) containing setting items corresponding to the function selected in the selection region B205 is provided, and a display region B207 for displaying a description of the selected function is provided below the button B206. Upon the button B206 being selected, a drop-down list is displayed in which setting items (measurement items) serving as parameters of the selected function are listed. The user displays the drop-down list by operating the input unit 53 and selecting the button B206, and selects one of the measurement items whose list is displayed in the drop-down list. In the example shown in FIG. 16, a measurement item "RBC" is selected.

Also, on the right of the button B206 and the display region B207, an operator input region B208 for inputting operators when the conditional expression is a logical expression and a numeric value input region B209 for inputting numeric values are provided. The operator input region B208 is provided with a plurality of buttons for selecting operators, and the numeric value input region B209 is provided with a plurality of buttons for inputting numeric values. The user can input the conditional expression that is a logical expression by selecting the buttons in the operator input region B208 and the numeric value input region B209.

The CPU 51a accepts the aforementioned user input of the conditional expression (IF part). Upon the conditional expression being input, the conditional expression is displayed in the display region B204. In the example in FIG. 16, the function "ItemValue (RBC[****10^4/uL])>4200" of the input conditional expression is displayed. Also, below the display region B207, a correction button B210, which can be selected, is provided. The correction button B210 is used to correct a function that is already input and displayed in the display region B204. When correcting a function, the user again operates the selection region B205, the button B206, and the buttons provided in the operator input region B208 and the numeric value input region B209, which are described above, to correct the function, and selects the correction button B207. Thus, correction of the function is executed, and the function after being corrected is displayed in the display region B204.

Below the selection region B205, a button B211 for displaying a drop-down list for setting an action (command) corresponding to the conditional expression is provided. The button B211 is provided in order to set the THEN part of a rule. The CPU 51a, upon accepting an input for selecting the button B211, displays a drop-down list of action commands that can be set.

Figure 17:
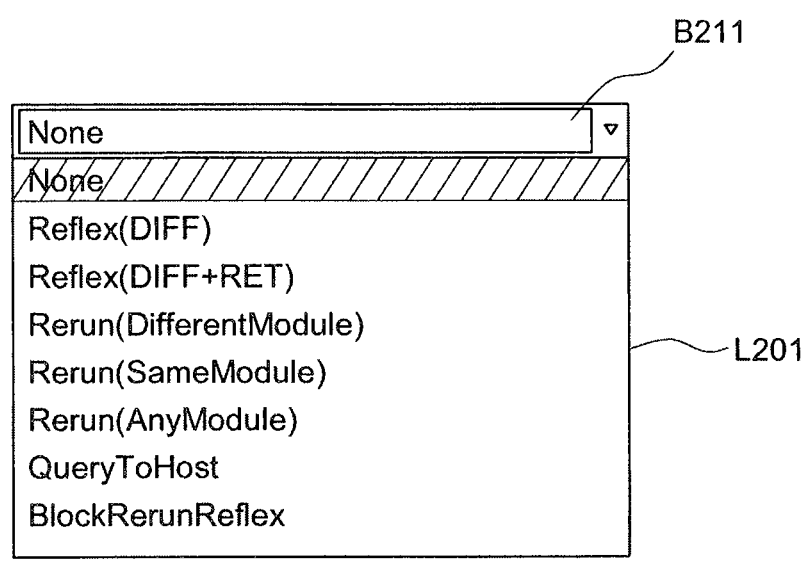
FIG. 17 is a diagram showing an example of display of a drop-down list for setting an action command.

FIG. 17 is a diagram showing an example of display of the drop-down list for setting an action command. As shown in FIG. 17, upon the button B211 being selected, a drop-down list L201 is displayed in which action commands including action commands "Reflex (DIFF)", "Reflex (DIFF+RET)", and "Reflex (RET)" for the reflex test, action commands "Rerun (DifferentModule)", "Rerun (SameModule)", and "Rerun (AnyModule)" for the rerun test, an action command "QueryToHost" for the host query, "None", and "BlockRerunReflex" are listed. The user can select a setting item (action command) from the drop-down list displayed as above. The CPU 51a accepts the aforementioned user input of (THEN part). In the example shown in FIG. 16, "QueryToHost" is selected as an action.

As shown in FIG. 16, below the button B211 in the rule registration dialog D201, an input box B212 for inputting a description (action comment) of the selected setting item (action) is provided. On the right of the input box B212, an importance selection region B213 for designating the importance of the input rule by three levels (high, middle, low) is provided. In the example shown in FIG. 16, the "low" importance is selected.

Also, a button B214 for checking whether or not the conditional expression displayed in the display region B204 is appropriate is provided between the display region B204 and the selection region B205. Upon the button B214 being selected, the CPU 51a determines whether the input conditional expression is related to a measurement item that is executable in terms of the configuration of this specimen analyzer, and whether the conditional expression is grammatically appropriate. If it is determined that the conditional expression is not appropriate, an icon (not shown) indicating that the rule is not appropriate is displayed on the left of the display region B204. In this case, the user corrects the conditional expression. On the other hand, if it is determined that the conditional expression is appropriate, an icon indicating that the rule is appropriate is displayed on the left of the display region B204. With the icon on the left of the display region B204, the user can readily determine whether the conditional expression is appropriate.

Below the importance selection region B213, an OK button B215 for executing registration of the input rule and a cancellation button B216 for cancelling the input content and closing the rule registration dialog D201 are provided. The user selects the OK button B215 when registering the input rule. Upon accepting an instruction to register or correct a rule from the user as described above (step S602), the CPU 51a registers the input rule in the rule database DB2 provided in the hard disk (step S603), closes the repeat rule correction dialog D301 or the rule registration dialog D201, displays the registered rule in the lower region A202 of the rule settings screen D3 (step S604), and ends the rule setting processing.

Figure 18:
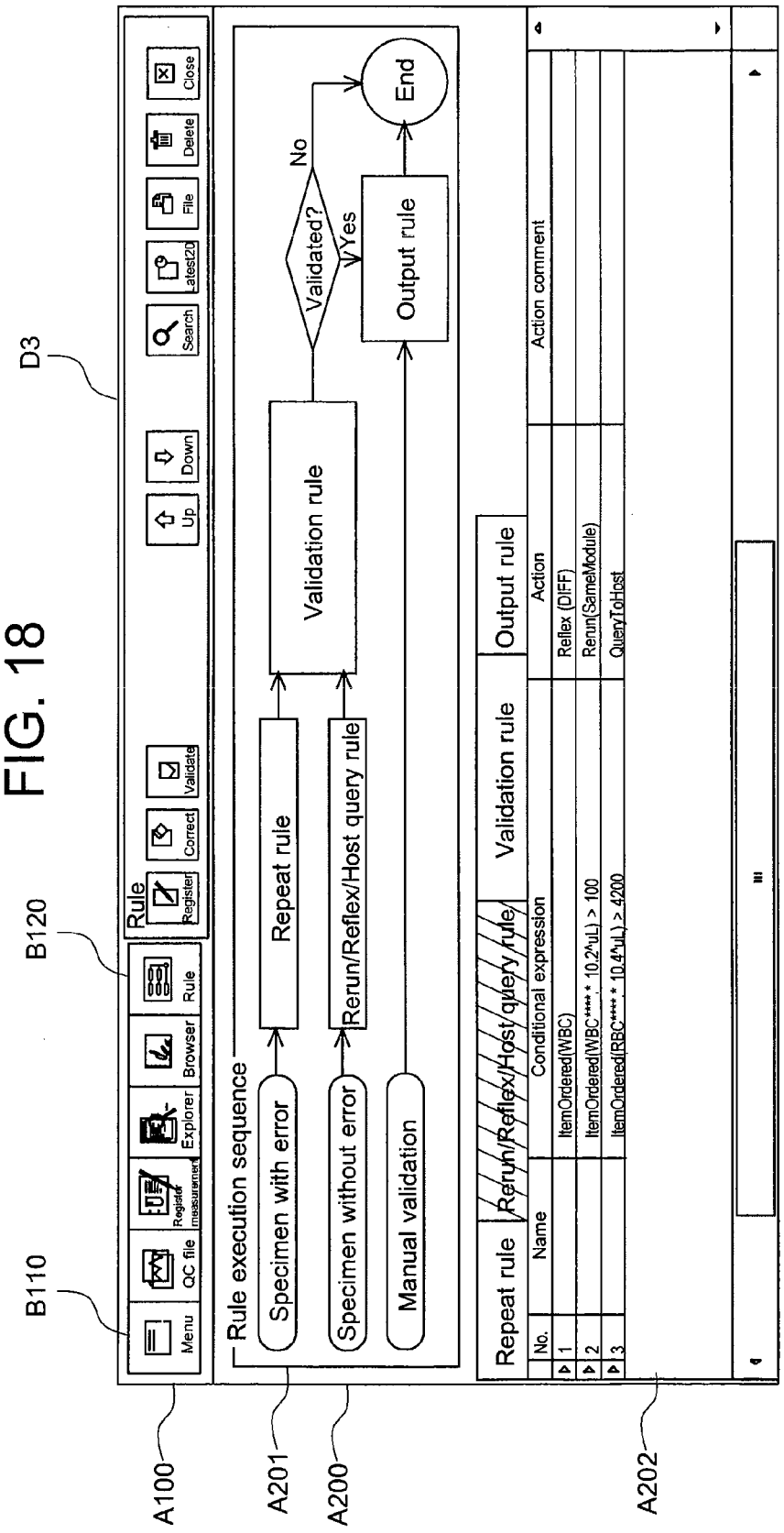
FIG. 18 is a diagram showing an example of the rule settings screen after rules are registered.

FIG. 18 is a diagram showing an example of the rule settings screen after the rule is registered. After the rule is registered, information (rule number, name, conditional expression, action, action comment) regarding the registered new rule is added in the lower region A202 of the rule settings screen D3. In the example shown in FIG. 18, the reflex rule having the rule number "1", the conditional expression "ItemOrdered (WBC)", and the action "Reflex (DIFF)", the rerun rule having the rule number "2", the conditional expression "ItemValue (WBC [****.*10^2/uL]> 100", and the action "Rerun (SameModule)", and the host query rule having the rule number "3", the conditional expression "ItemValue (RBC[****10^4/uL]>4200", and the action "QueryToHost" are registered.

Next, a description will be given for a measurement operation and screen display in the case were the rules shown in FIG. 18 are registered. When the specimen is measured and the measurement data is analyzed by the information processing unit, it is determined whether or not a measured value regarding WBC exceeds a reference value "100". At this time, if it is determined that the measured value regarding WBC exceeds the reference value "100", the value of the function "ItemValue(WBC[****.*10^2/uL]> 100" is "True". Such an analysis result with the value of "ItemValue(WBC[****.*10^2/uL]>100" being "True" matches the conditional expression of the rule with the rule number "2". Accordingly, the CPU 51a executes the action "Rerun (SameModule)", which is the THEN part of the rule with the rule number "2". As a result of execution of the action "Rerun (SameModule)", remeasurement of the specimen is performed regarding the same discrete item as that in the initial examination by the measurement unit that executed the initial examination.

Also, when the measurement data is analyzed by the information processing unit, it is determined whether or not a measured value regarding RBC exceeds a reference value "4200". If it is determined here that the measured value regarding RBC exceeds the reference value "4200", the value of the function "ItemValue(RBC[**10^4/uL]> 4200" is "True". Such an analysis result with the value of the function "ItemValue(RBC[**10^4/uL]>4200" being "True" matches the conditional expression of the aforementioned host query rule with the rule number "3". Accordingly, if the analysis result matches neither of the aforementioned conditional expressions corresponding to the rule numbers "1" and "2", the CPU 51a executes the action "QueryToHost", which is the THEN part of this rule. As a result of execution of the action "QueryToHost", a rule result "QueryToHost" is registered, and a request to determine the necessity of remeasurement is given to the examination information management device 500.

Figure 19:
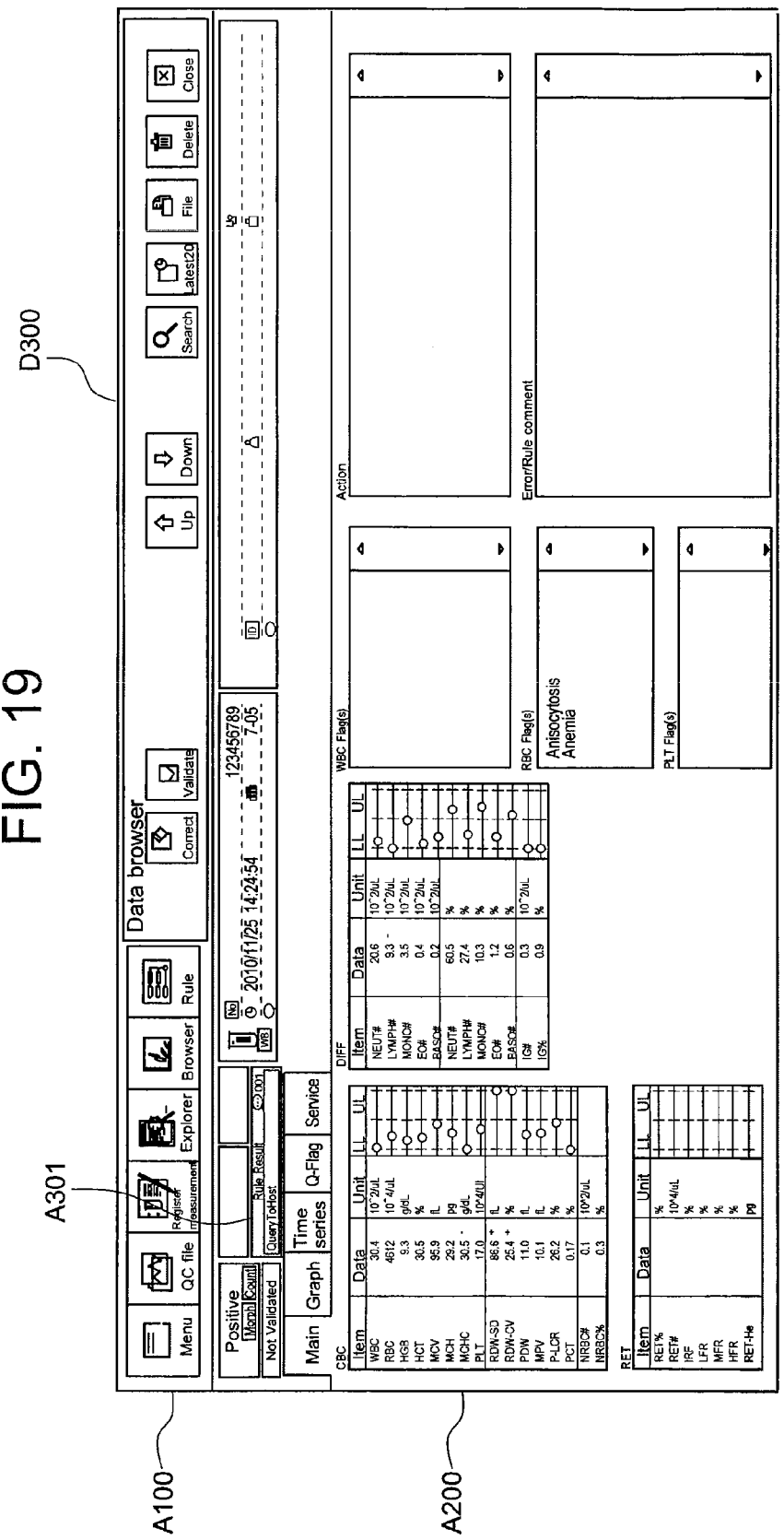
FIG. 19 is a diagram showing an example of an analysis result details screen.

The specimen analysis result is displayed by the information processing unit 5. FIG. 19 is a diagram showing an example of an analysis result details screen. If the conditional expression of the aforementioned host query rule is matched, an analysis result shown in FIG. 19 is displayed. An analysis result details screen D300 is provided with a "Rule Result" display region A301. If the analysis result matches the host query rule and the action "QueryToHost" is executed, "QueryToHost" is displayed in the display region A301. It can be thus recognized that a query about the determination of the necessity of remeasurement of the specimen has been made to the examination information management device 500.

Also, the information processing unit 5 can display a specimen information list screen. FIG. 20 is a diagram showing an example of the specimen information list screen. As shown in FIG. 20, the specimen information list screen D400 is provided with a region A401 in which a list of specimen information that has undergone analysis is displayed, and a region A402 in which an analysis result is displayed regarding a specimen, which is selected from among the specimens whose specimen information is displayed in the region A401. The region A401 is provided with a display item "rule result", and "QueryToHost" is displayed in the display item "rule result" for the specimen information that matches the aforementioned host query rule. This means that the specimen was determined to be a subject of host query as a result of rule determination. If the user checks this specimen information list screen D400 and further wants to know what kind of rule is applied, he/she can check the details of the content thereof by displaying the aforementioned analysis result details screen D300.

As described above in detail, the specimen analysis system according to the present embodiment has a configuration in which the specimen analyzer 100 executes processing for transmitting a result of measurement of a specimen by a measurement unit to the examination information management device 500, processing for making a query to the examination information management device 500 about whether or not remeasurement of the specimen is necessary, and processing for determining whether or not the measurement result matches a predetermined condition stored in advance in the specimen analyzer 100, and if the measurement result matches the predetermined condition, the specimen analyzer 100 causes the measurement unit to execute remeasurement of the specimen. With this configuration, depending on the specimen, remeasurement can be executed based on the measurement result of the measurement unit, without receiving a result of the determination of the necessity of remeasurement from the examination information management device 500. It is therefore possible to suppress occurrence of a delay in remeasurement of a specimen due to a processing state of the examination information management device 500 or a state of communication between the specimen analyzer 100 and the examination information management device 500, and to execute remeasurement of the specimen more quickly.

Also, in the specimen analysis system according to the present embodiment, a user can set the repeat rule, the rerun rule, the reflex rule, and the host query rule. With this configuration, the user can freely set rules that are suitable for his/her own facility, resulting in improvement of convenience for the user.

Also, in the specimen analysis system according to the present embodiment, the rerun rule and the reflex rule have a higher priority over the host query rule, and if an analysis result matches a condition of the rerun rule or the reflex rule, host query is not executed even if it matches a condition of the host query rule, but the rerun test or the reflex test is executed. With this configuration, if it is determined by the rerun rule or the reflex rule that remeasurement is necessary, further determination of the necessity of remeasurement is not performed by the examination information management device 500, and a load on the examination information management device 500 can be further suppressed.

Other Embodiments

Note that in the above embodiment, when the examination information management device 500 accepts a request to determine the necessity of remeasurement of a specimen from the specimen analyzer 100, it determines the necessity of remeasurement and transmits the determination result to the specimen analyzer 100 regardless of the necessity of remeasurement. However, the present invention is not limited thereto. The examination information management device 500 may determine the necessity of remeasurement upon receiving a result of measurement of a specimen from the specimen analyzer 100, and may transmit the determination result to the specimen analyzer 100 only when it determines that remeasurement is necessary.

Also, although the above embodiment described a configuration in which all of the rerun rules, reflex rules, and host query rules that are registered in the rule database DB2 are executed when a specimen analysis result is obtained, the present invention is not limited thereto. The rerun rule has a higher priority over the reflex rule, and the reflex rule has a higher priority over the host query rule. Accordingly, an alternative configuration may be employed in which if it is determined by the rerun rule that the rerun test needs to be executed, the reflex rule and the host query rule are not executed, and if it is determined by the reflex rule that the reflex test needs to be executed, the host query rule is not executed.

Also, an alternative configuration may be employed in which even in the case where an analysis result matches the condition of the rerun rule or the reflex rule, the specimen analyzer executes host query if the analysis result matches the condition of the host query rule.

Also, the above embodiment described a configuration in which if a plurality of action commands for the reflex test are registered as a result of execution of a plurality of reflex rules, remeasurement is performed regarding all measurement items (discrete item) designated in all registered action commands for the reflex test. However, the present invention is not limited thereto. An alternative configuration may be employed in which if a plurality of action commands for the reflex test are registered as a result of execution of a plurality of reflex rules, remeasurement is performed regarding only measurement items (discrete item) designated in part of the registered action commands for the reflex test.

Also, if an analysis result does not match any of the aforementioned repeat rule, rerun rule, reflex rule, and host query rule, host query may be executed.

Also, although the above embodiment described an example in which the present invention is applied to a multichannel blood cell counter, the present invention is not limited thereto. The present invention may also be applied to a specimen analyzer other than a multichannel blood cell counter, such as a blood coagulation measurement device, an immunoassay device, a urine formed element analyzer, a urine quantitative analyzer, or a biochemical analyzer.

Also, although the above embodiment described a configuration in which all processing of the computer program 54a is executed by a single computer 5a, the present invention is not limited thereto. A distributed system can also be employed in which processing similar to the above-described computer program 54a is distributed to and executed by a plurality of devices (computers).

The specimen analysis system, the specimen analyzer, and the specimen analysis method of the present invention are useful as a specimen analysis system, a specimen analyzer, and a specimen analysis method for analyzing a specimen.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A specimen analysis system comprising:
   an examination information management device for managing examination information regarding examination of a specimen; and
   a specimen analyzer for measuring the specimen and transmitting a measurement result to the examination information management device,
   the specimen analyzer comprising:
      a measurement unit configured to measure the specimen,
      a storage unit configured to store a first determination condition for determining an execution of remeasurement of the specimen and a second determination condition for determining an execution of a query about remeasurement of the specimen, and
      a control unit in communication with the measurement unit and the storage unit, the control unit configured to:
      cause the measurement unit to execute measurement of the specimen,
      transmit a measurement result of the specimen to the examination information management device,
      determine whether or not the measurement result of the specimen matches the first determination condition,
      responsive to a determination that the measurement result matches the first determination condition, cause the measurement unit to execute remeasurement of the specimen and transmit a remeasurement result of the specimen to the examination information management device,
      responsive to a determination that the measurement result does not match the first determination condition, determine whether or not the measurement result of the specimen matches the second determination condition, and
      responsive to a determination that the measurement result matches the second determination condition, transmit a query about remeasurement of the specimen to the examination information management device, wherein the examination information management device is remote from the specimen analyzer.

2. The specimen analysis system according to claim 1, wherein the examination information management device is configured to determine a necessity of remeasurement and transmit the determination information, which is a determination result, to the specimen analyzer in a case of accepting the query about remeasurement of the specimen from the specimen analyzer.

3. The specimen analysis system according to claim 2, wherein when the examination information management device has accepted the measurement result of the specimen and has not accepted the query about remeasurement of the specimen from the specimen analyzer, the examination information management device is configured not to determine the necessity of remeasurement based on the result of measurement of the specimen.

4. The specimen analysis system according to claim 1, wherein the examination information management device, upon receiving the measurement result of the specimen and the query about remeasurement of the specimen from the specimen analyzer, determines whether or not remeasurement of the specimen is necessary, and transmits the determination information indicating that remeasurement is necessary to the specimen analyzer only in a case where remeasurement is necessary.

5. The specimen analysis system according to claim 1, wherein the measurement unit measures the specimen, which is collected from an object to be examined, and acquires the measurement result,
the examination information management device stores, as the examination information, a past measurement result, which is a result of past measurement of the object to be examined and is acquired prior to the first measurement result, and
the first determination condition stored in the storage unit is a determination condition for determining whether or not remeasurement of the specimen is necessary based on the measurement result, without using the past measurement result.

6. The specimen analysis system according to claim 5, wherein the examination information management device determines whether or not remeasurement of the specimen is necessary based on the measurement result received from the specimen analyzer and the past measurement result stored in the examination information management device.

7. The specimen analysis system according to claim 1, wherein the control unit causes the measurement unit to execute remeasurement of the specimen when the control unit receives, from the examination information management device, determination information indicating that remeasurement of the specimen is necessary.

8. A specimen analyzer that is communicably connected to an examination information management device for managing examination information regarding examination of a specimen, comprising:
   a measurement unit configured to measure the specimen;
   a storage unit configured to store a first determination condition for determining an execution of remeasurement of the specimen and a second determination condition for determining an execution of a query about remeasurement of the specimen; and a control unit in communication with the measurement
unit and the storage unit, the control unit configured to:
cause the measurement unit to execute measurement of
the specimen,
transmit a measurement result of the specimen to the
examination information management device,
determine whether or not the measurement result of the
specimen matches the first determination condition,
responsive to a determination that the measurement
result matches the first determination condition,
cause the measurement unit to execute remeasurement of the specimen and transmit a remeasurement
result of the specimen to the examination information management device,
responsive to a determination that the measurement
result does not match the first determination condition, determine whether or not the measurement
result of the specimen matches the second determination condition, and
responsive to a determination that the measurement
result matches the second determination condition,
transmit a query about remeasurement of the specimen to the examination information management
device, wherein the examination information management device is remote from the specimen analyzer.

9. The specimen analyzer according to claim 8,
wherein the measurement unit measures the specimen,
which is collected from an object to be examined, and
acquires the measurement result,
the examination information management device stores,
as the examination information, a past measurement
result, which is a result of past measurement of the
object to be examined and is acquired prior to the
measurement result, and
the first determination condition stored in the storage unit
is a determination condition for determining whether or
not remeasurement of the specimen is necessary based
on the measurement result, without using the past
measurement result.

10. The specimen analyzer according to claim 8, further
comprising:
an input unit for accepting an input from a user,
wherein the control unit is configured to be able to accept
change of the first determination condition or the
second determination condition, by the input unit, and
to set the accepted first determination condition or
second determination condition.

11. The specimen analyzer according to claim 8,
wherein the first determination condition includes a first
remeasurement condition and a second remeasurement
condition, and
in a case where the measurement result matches the first
remeasurement condition, the control unit causes the
measurement unit to execute remeasurement of the
specimen regarding a first measurement item, which is
the same as a first measurement item for the specimen
that was measured by the measurement unit, and in a
case where the measurement result matches the second
remeasurement condition, the control unit causes the
measurement unit to execute remeasurement of the
specimen regarding a second measurement item, which
is different from the first measurement item for the
specimen that was measured by the measurement unit.

12. The specimen analyzer according to claim 11,
wherein in a case where the measurement result matches
the second remeasurement condition, the control unit is
configured to cause the measurement unit to execute
remeasurement of the specimen regarding the first
measurement item and the second measurement item.

13. The specimen analyzer according to claim 11,
wherein the control unit is configured to be able to accept
designation of the second measurement item, by the
input unit.

14. The specimen analyzer according to claim 8, comprising:
a plurality of measurement units; and
an input unit for accepting an input from a user,
wherein the control unit is able to accept designation of a
measurement unit for executing remeasurement of the
specimen, by the input unit.

15. The specimen analyzer according to claim 8, further
comprising:
a display unit,
wherein in a case of executing the query about remeasurement of the specimen, the control unit is configured
to cause the display unit to display information indicating that the control unit has made a query to the
examination information management device, along
with the result of measurement of the specimen.

16. The specimen analyzer according to claim 8,
wherein the control unit is configured to determine
whether or not a predetermined abnormality has
occurred in the measurement unit during a specimen
measurement operation by the measurement unit, and
to cause the measurement unit to execute remeasurement of the specimen regardless of the measurement
result in a case where it is determined that the predetermined abnormality has occurred.

17. The specimen analyzer according to claim 16, comprising:
a plurality of measurement units,
wherein in a case where it is determined that the predetermined abnormality has occurred in a measurement
unit that executed the specimen measurement operation, the control unit is configured to cause the measurement unit that executed the measurement to
execute remeasurement of the specimen.

18. The specimen analyzer according to claim 8,
wherein the control unit causes the measurement unit to
execute remeasurement of the specimen when the control unit receives, from the examination information
management device, determination information indicating that remeasurement of the specimen is necessary.

19. A specimen analysis method for analyzing a specimen
using a specimen analyzer that is communicably connected
to an examination information management device for managing examination information regarding examination of the
specimen, the method comprising:
measuring a specimen and acquiring a measurement result
of the specimen;
transmitting the measurement result to the examination
information management device;
determining whether or not the measurement result
matches a first determination condition for determining
an execution of remeasurement of the specimen;
responsive to a determination that the measurement result
matches the first determination condition, executing
remeasurement of the specimen and transmitting a
remeasurement result of the specimen to the examination information management device;
responsive to a determination that the measurement result
does not match the first determination condition, determining whether or not the measurement result of the specimen matches a second determination condition for determining an execution of a query about remeasurement of the specimen; and responsive to a determination that the measurement result matches the second determination condition, transmitting a query about remeasurement of the specimen to the examination information management device, wherein the examination information management device is remote from the specimen analyzer.

20. The specimen analysis method according to claim 19, further comprising:

responsive to a reception of determination information indicating that remeasurement of the specimen is necessary, from the examination information management device, executing remeasurement of the specimen.

\* \* \* \* \*